(12) United States Patent
Shan

(10) Patent No.: US 10,328,430 B2
(45) Date of Patent: Jun. 25, 2019

(54) DISPOSABLE SEALED BODY FLUID RETENTION DEVICE AND CONVENIENT AND SANITARY FLUID-TAKING METHOD

(71) Applicant: WUXI KAISHUN MEDICAL DEVICE MANUFACTURING CO., LTD., Wuxi, Jiangsu (CN)

(72) Inventor: Xijie Shan, Wuxi (CN)

(73) Assignee: WUXI KAISHUN MEDICAL DEVICE MANUFACTURING CO., LTD., Wuxi, Jiangsu (CN)

( * ) Notice: Subject to any disclaimer, the term of this patent is extended or adjusted under 35 U.S.C. 154(b) by 223 days.

(21) Appl. No.: 15/126,170

(22) PCT Filed: Mar. 13, 2015

(86) PCT No.: PCT/CN2015/074219
§ 371 (c)(1),
(2) Date: Sep. 14, 2016

(87) PCT Pub. No.: WO2015/135504
PCT Pub. Date: Sep. 17, 2015

(65) Prior Publication Data
US 2017/0095815 A1  Apr. 6, 2017

(30) Foreign Application Priority Data

Mar. 14, 2014  (CN) .......................... 2014 1 0095859
Mar. 14, 2014  (CN) ..................... 2014 2 0117108 U
Jun. 13, 2014  (CN) .......................... 2014 1 0263574

(51) Int. Cl.
*B01L 3/00* (2006.01)
*A61B 10/00* (2006.01)

(52) U.S. Cl.
CPC ........ *B01L 3/50825* (2013.01); *A61B 10/007* (2013.01); *B01L 2200/026* (2013.01); *B01L 2200/087* (2013.01); *B01L 2300/048* (2013.01)

(58) Field of Classification Search
CPC ........... B01L 3/50825; B01L 2200/087; B01L 2300/048; B01L 2200/026; B67C 2011/30; A61B 10/007
(Continued)

(56) References Cited

U.S. PATENT DOCUMENTS 2,850,050 A * 9/1958 Connolly ............. A61B 10/007
141/126
4,064,760 A  12/1977  Benjamin
2011/0306899 A1 * 12/2011 Brown ............... A61B 5/15003
600/581

FOREIGN PATENT DOCUMENTS

CN  2249407  3/1997
CN  201168103  12/2008
(Continued)

OTHER PUBLICATIONS

International Search Report for PCT/CN2015/074219 dated Jun. 8, 2015, 3 pages.

*Primary Examiner* — Robert R Raevis
(74) *Attorney, Agent, or Firm* — Nixon & Vanderhye P.C.

(57) ABSTRACT

Disclosed is a disposable sealed body fluid retention device, comprising a fluid storage pipe (1), a fluid-taking piece (2) and a shielding body (4), wherein the fluid storage pipe (1) comprises an opening part (11) and a fluid storage cavity (12); the fluid-taking piece (2) is provided with a fluid guide channel (21), an exhaust channel (22), an annular side wall (23) and a partition (28); the partition (28) is located in the annular side wall (23) and separates the fluid guide channel (21) from the exhaust channel (22); one end of the fluid guide channel (21) is provided with a fluid inlet (24) and the other end is provided with a fluid outlet (25); the fluid outlet (25) is located at the lower part of the fluid-taking piece (2); one end of the exhaust channel (22) is provided with an exhaust port (26) and the other end is provided with an air outlet (27); the exhaust port (26) is located at the lower part of the fluid-taking piece (2); and the shielding body (4) is (Continued)

located outside the fluid storage pipe (1). The disposable sealed body fluid retention device has the advantages of convenience and sanitation, and when removing the fluid-taking piece (2) and the shielding body (4), it is ensured that the outer wall of the fluid storage pipe (1) is not contaminated with urine and the fluid storage pipe (1) can be directly used for a urine dipstick test and urine analyser detection.

14 Claims, 15 Drawing Sheets

(58) Field of Classification Search
USPC .......... 73/863, 864, 864.51, 864.59, 864.63, 73/864.91; 141/97, 285, 289, 290, 295, 141/297, 299
See application file for complete search history.

(56) References Cited

FOREIGN PATENT DOCUMENTS

| | | |
|---|---|---|
| CN | 201335785 | 10/2009 |
| CN | 201558706 | 8/2010 |
| CN | 202002824 | 10/2011 |
| CN | 202770672 | 3/2013 |
| CN | 202994542 | 6/2013 |
| CN | 203561531 | 4/2014 |
| CN | 2039166 M | 11/2014 |
| CN | 203916685 | 11/2014 |
| CN | 203944399 | 11/2014 |
| CN | 203944400 | 11/2014 |
| CN | 204034726 | 12/2014 |
| JP | 3178921 | 10/2012 |

* cited by examiner

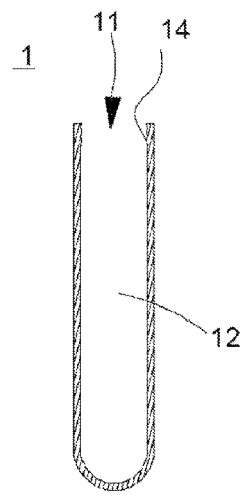
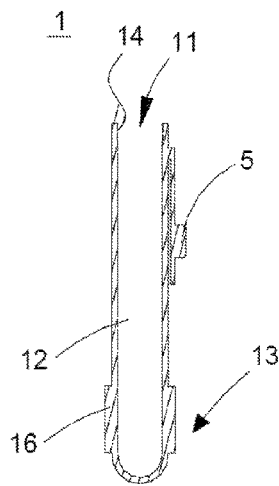
Figure 3    Figure 4
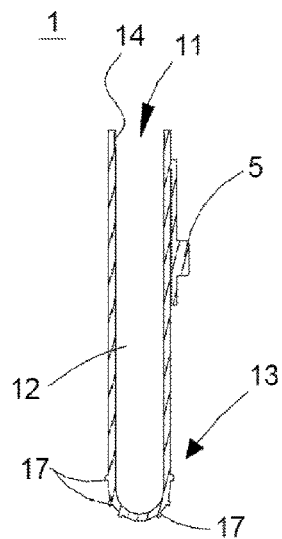
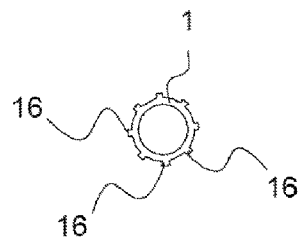
Figure 5    Figure 6
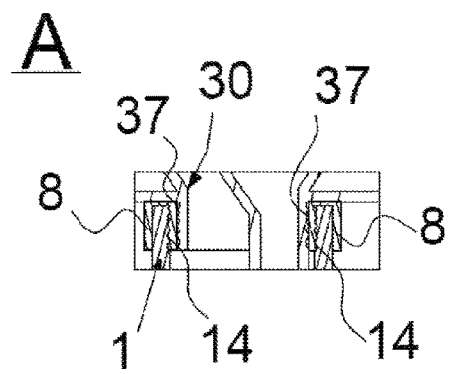
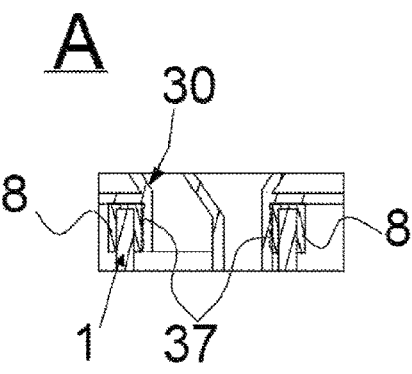
Figure 7    Figure 8

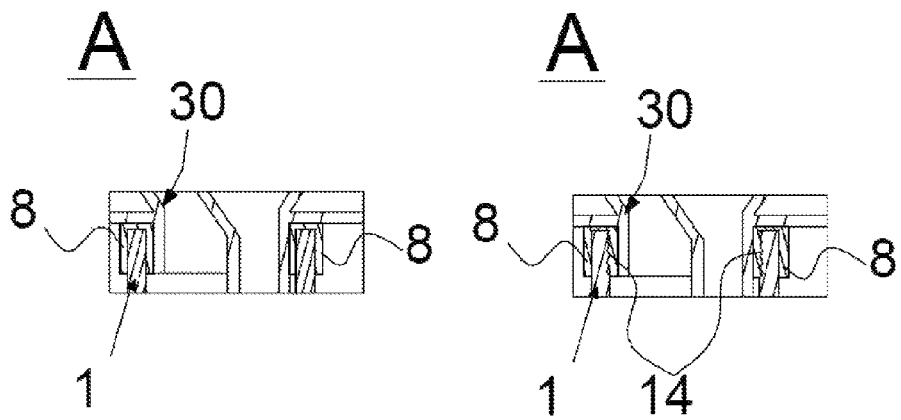
Figure 9
Figure 10
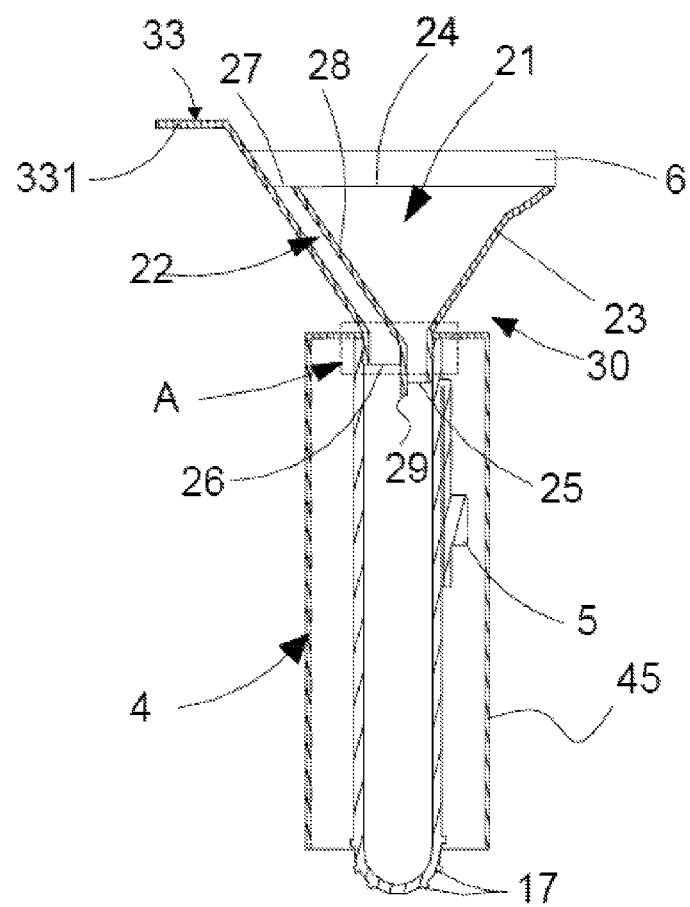
Figure 11

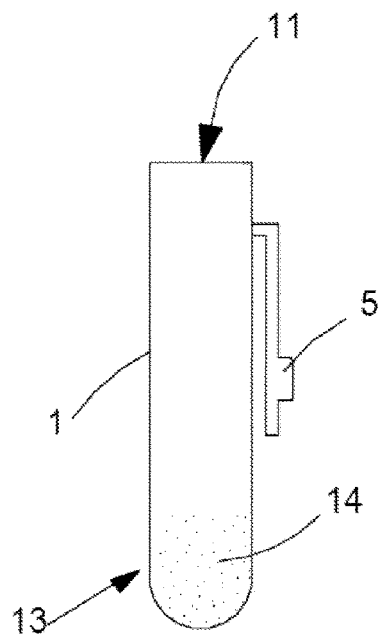
Figure 26
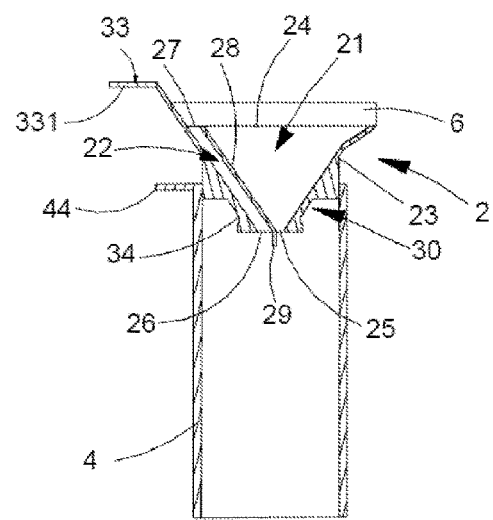
Figure 27
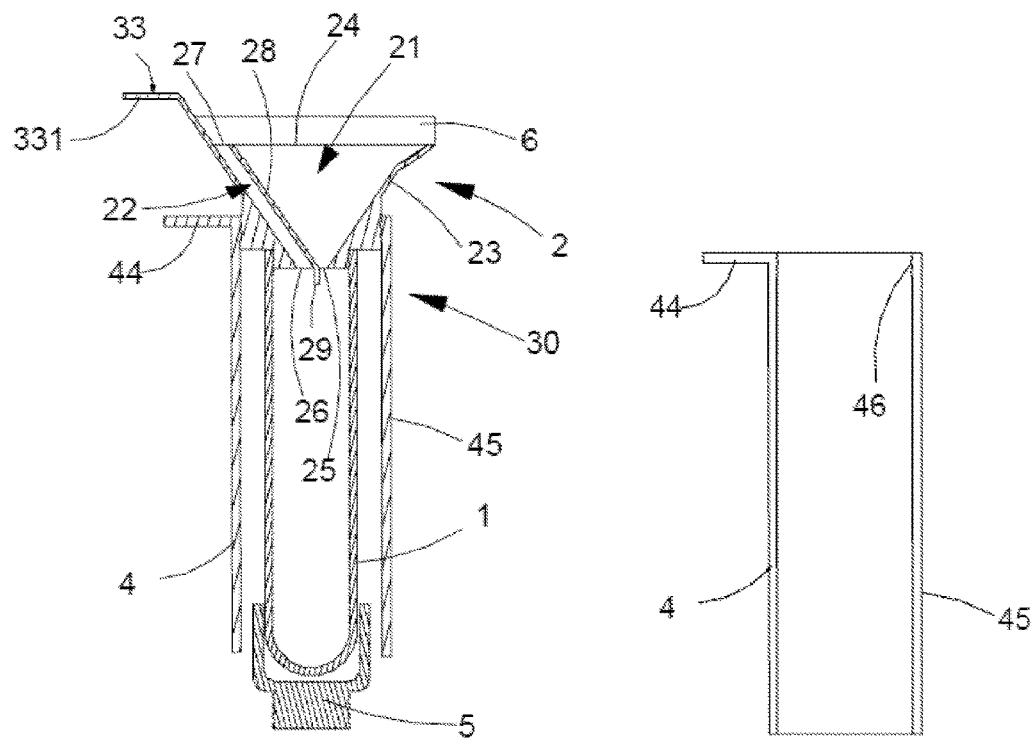
Figure 28
Figure 29

DISPOSABLE SEALED BODY FLUID RETENTION DEVICE AND CONVENIENT AND SANITARY FLUID-TAKING METHOD

This application is the U.S. national phase of International Application No. PCT/CN2015/074219 filed 13 Mar. 2015 which designated the U.S. and claims priority to CN patent application No. 201410095859.5 filed 14 Mar. 2014, CN 201420117108.4 filed 14 Mar. 2014 and CN 201410263574.8 filed 13 Jun. 2014, the entire contents of each of which are hereby incorporated by reference.

TECHNICAL FIELD

The present disclosure relates to medical equipment, and particularly to a fluid collecting device for collecting fluid such as urine in a laboratory and a pathological analysis center of hospital, and more particularly to a disposable sealed body fluid retention device and a convenient and sanitary fluid collecting method.

TECHNICAL BACKGROUND

Urine analysis results can provide information used for predicting diseases of visceral organs and determining the current health conditions of the tested subjects, and therefore are generally employed for testing urine samples from numerous patients, subjects under physical examination, hospitalized subjects and the like in many hospitals and laboratory centers.

Typically, the tested subjects are required to collect their urine samples with paper cups in the rest room, and then place the paper cups on a specified bracket in the laboratory or transfer the urine samples into specified test tubes. After being collected in the laboratory and so on, the urine samples are analyzed in another laboratory.

In most cases, lots of urine samples are necessarily analyzed completely within one day. However, these opening paper cups disposed side by side occupy a large space until the completion of the analysis. Further, when being sent to the laboratory, the urine samples in the paper cups might be somewhat lost due to possible unintentional fall or tilting of the paper cups, thus causing environment pollution and waste of the urine samples. Moreover, the urine samples are collected by most tested subjects in a volume much higher than that as actually required, thus so many urine samples together smell badly, resulting in comfortability degradation of the working environment, as well as lowered working efficiency of doctors, nurses and other personnel for the urine analysis.

As can be seen from the above, the conventional urine collecting method is defective. For example, it is difficult for some tested subjects to excrete urine into the paper cup, thus sometimes excreting urine on the clothes or hands. Or, the outer wall of the test tube or fluid storage tube is stained by the urine when the urine is being transferred to the test tube, as a result, the stained test tube or fluid storage tube containing the urine cannot be directly put into a urine analysis instrument, instead the urine needs to be transferred again into a clean test tube or fluid storage tube. Therefore, the above-mentioned urine collecting method is defective in terms of sanitation.

Therefore, there is a need for a fluid collecting device, which has a simple design and structure and is convenient in operation, used for collecting and transferring urine into the designated container safely and conveniently without staining the outer wall of the test tube or fluid storage tube.

SUMMARY

Accordingly, an aspect of the present disclosure is to provide a fluid collecting device, which is capable of conveniently and safely guiding urine into the specified container and maintaining cleanness and sanitation of the outer wall of the container during a urine collecting process, so that the container containing the urine can be directly used for testing by test paper and instrument.

An aspect of the present disclosure is implemented by:
a disposable sealed body fluid retention device including: a fluid storage tube, a fluid-taking piece and a shielding body, where the fluid storage tube includes an opening and a fluid storage cavity; the fluid-taking piece is fixed to the fluid storage tube; the fluid-taking piece includes a fluid guiding passage, an air exhaust passage, an annular side wall and a spacer; the spacer is located in the annular side and configured to separate the fluid guiding passage from the air exhaust passage; the fluid guiding passage has one end as a liquid inlet and the other end as a liquid outlet; the liquid outlet is located at a lower part of the fluid-taking piece; the air exhaust passage has one end as an air outlet and the other end as an air exhaust opening; the air exhaust opening is located at the lower part of the fluid-taking piece; and the shielding body is posited at the outside of the fluid storage tube and configured to prevent body fluid from being spurting on an outer wall of the fluid storage tube.

Further, the lower part of the fluid-taking piece is fixedly connected to the opening of the fluid storage tube.

In the case where the fluid-taking piece is connected to the fluid storage tube by threads or rotatable snap, external threads are provided on the outer wall of the lower part of the fluid-taking piece, internal threads are provided on the inner wall of the opening of the fluid storage tube, and the fluid-taking piece is detachably connected with the fluid storage tube through threads.

In the case where the lower part of the fluid-taking piece is insertedly connected to the opening of the fluid storage tube, the lower part of the fluid-taking piece is insertedly connected to the opening of the fluid storage tube directly or through a sealing ring disposed between the lower part of the fluid-taking piece and the opening of the fluid storage tube, where the sealing ring is at least attached to the inner wall of the opening of the fluid storage tube and the top of the fluid storage tube, or the sealing ring may be mounted onto the opening of the fluid storage tube. During inserting, the lower part of the fluid-taking piece tightly matches with the sealing ring mounted onto the opening of the fluid storage tube.

For the inserting of the fluid-taking piece onto the fluid storage tube, the sealing ring is made of elastic material, so that the sealing ring not only has a function of sealing but also facilitates the inserting/removing of the fluid-taking piece onto/from the fluid storage tube.

Further, the shielding body includes a shielding side wall surrounding the fluid storage tube at an angle equal to or less than 360°. The shielding side wall functions to prevent the fluid storage tube from being stained by urine to the maximum extent.

When the shielding side wall surrounds the fluid storage tube at an angle of 0°, the shielding side wall has a flat shape.

When the shielding side wall surrounds the fluid storage tube at an angle less than 360°, the shielding side wall has a C shape.

When the shielding side wall surrounds the fluid storage tube at an angle equal to 360°, the shielding side wall has a tubular shape. The shielding body further includes a bottom plate provided to the bottom of the shielding side wall, and the bottom plate may be formed in one piece with the shielding side wall, or the bottom plate and the shielding side wall may be formed separately and then connected. When the bottom plate is formed in one piece with the shielding side wall, the shielding body has a cylindrical shape. When the bottom plate and the shielding side wall are formed separately and then connected, the shielding body may be formed in one piece with the fluid-taking piece, or the shielding body may be connected to the fluid-taking piece.

The shielding side wall may further surround the fluid storage tube at an angle larger than 360°, so that some of the shielding side wall overlaps.

The shielding body may be assembled by some components. For example, the shielding body includes a first component and a second component, which may be fixedly connected. The first component may be formed in one piece with the fluid-taking piece, or may be fixedly connected with the fluid-taking piece.

The shielding body may be fixedly connected with the fluid-taking piece by way of threads, clip snap, rotatable snap, fastening, interference fit, or magnetic adsorption, or may be formed in one piece with the fluid-taking piece. Alternatively, the shielding body may be fixedly connected to the fluid storage tube, for example, the fluid storage tube is directly inserted into the shielding body, or the shielding body is fixed to the fluid storage tube by way of threads, clip snap, rotatable snap, or magnetic adsorption. Alternatively, the shielding body may be fixedly connected to the connector by way of threads, clip snap, rotatable snap, or magnetic adsorption, for example. The shielding body may be formed in one piece with the connector.

In the case where the shielding body is fixedly connected to the fluid storage tube or the fluid-taking piece, the shielding body may be made of flexible material.

The shielding body has a tubular shape, a C shape or a flat shape. In the case where the shielding body is fixedly connected to the fluid-taking piece or the connector, a skidproof structure such as skidproof patterns may be provided on the lower part of the liquid storage tube, to facilitate the separation of the fluid storage tube from the connector.

There may be one or more (such as 1, 2, or 3) air exhaust openings of the air exhaust passages of the fluid-taking piece. In the case of a plurality of the air exhaust openings, the air exhaust openings may be arranged in different planes. The air exhaust opening and the liquid outlet may be arranged in the same plane or in different planes. Alternatively, at least one air exhaust opening is arranged in the same plane as the liquid outlet. The air exhaust opening may be located at the bottom of the liquid-taking piece, or the air exhaust opening may be located at the side surface of the air exhaust passage. Further, the disposable sealed body fluid retention device may further include a spacer extension located between the air exhaust opening and the liquid outlet. The spacer extension may be extended downwards from the spacer and formed in one piece with the spacer, or may be formed separately from the spacer, to prevent liquid leading to the liquid outlet from entering into the air exhaust opening.

The fluid storage tube may be a polygonal tube, for example, a pentagonal tube, a hexagonal tube or an octagonal tube. Alternatively, only the lower part of the fluid storage tube has a cross section of a polygonal shape. A skidproof structure may be provided at the lower part of the liquid storage tube. For example, longitudinal ribs, such as 2, 3, 4, 5, 6, 7 or 8 ribs, are arranged on the outer wall of the lower part of the fluid storage tube. Alternatively, a plurality of protrusions, coarse surfaces or skidproof patterns are arranged on the outer wall of the lower part of the fluid storage tube, which is not limited herein. The skidproof structure is configured for easy holding of the liquid storage tube being separated from the fluid-taking piece and for easy applying of forces to separate the fluid-taking piece from the liquid storage tube.

Further, a liquid collecting plate, which is used for collecting urine into the fluid guiding passage and avoiding spurting of the urine to outside of the fluid-taking piece during the urine collecting process, is fixed to the top of the annular side wall of the fluid-taking piece. The fluid-taking piece includes a handle for holding by hand. The liquid collecting plate may be arranged at both sides of the handle of the fluid-taking piece, or at either side of the handle. Alternatively, the liquid collecting plate may be omitted. An anti-spurting layer may be disposed on the annular side wall of the fluid guiding passage or the spacer to effectively absorb the impact by the urine in the fluid-taking process, thereby eliminating urine spurted to the outside of the fluid-taking piece. The anti-spurting layer may be made of a material with a porous surface.

The body fluid retention device may further include a connector including an axial through hole, the lower part of the fluid-taking piece is fixedly connected to the through hole of the connector, and the connector is fixedly connected to the opening of the fluid storage tube. The lower part of the fluid-taking piece may be connected to the through hole of the connector by threads, rotatable snap, interference fit, fastening, or insertion, which is not limited herein. Or, the lower part of the fluid-taking piece may be connected to the through hole of the connector by adhesive, so that the lower part of the fluid-taking piece is fixedly connected to the through hole of the connector. The connector may be detachably connected to the fluid storage tube by threads, rotatable snap, or insertion, which is not limited herein.

The connector is advantageous for simplifying the manufacturing of the fluid-taking piece. Particularly, the fluid-taking piece has been separated into two portions which match each other, to facilitate the manufacturing and assembling of the fluid-taking piece. Meanwhile, the connector is made of elastic material such as silicone, rubber and TPE (Thermoplastic Elastomer), which is advantageous for sealing and each inserted connection between the connector and the opening of the fluid storage tube as well as between the connector and the lower part of the fluid-taking piece.

Further, the disposal sealed body fluid retention device may further include a plug part, which is configured to match with the through hole of the connector or the opening of the fluid storage tube after the fluid-taking piece is removed, to isolate the fluid storage cavity from the outside.

In the case where the connector is fixedly connected to the lower part of the fluid-taking piece, the connector may be detachably connected to the fluid storage tube. When the fluid-taking piece is removed, the connector is removed together, and the plug part is directly mounted onto the opening of the fluid storage tube.

In the case where the connector is movably connected to the lower part of the fluid-taking piece, it is possible to merely remove the fluid-taking piece and maintain the connection between the connector and the fluid storage tube, and in this case, the plug part is mounted onto the through hole of the connector. Alternatively, it is possible to remove the connector along with removing the fluid-taking piece, and in this case, the plug part is mounted onto the opening of the fluid storage tube. Here, the plug part may be formed in one piece with the connector.

When the connector is omitted, the lower part of the fluid-taking piece is sealedly connected to the opening of the fluid storage tube, but this is not always necessary. For example, the lower part of the fluid-taking piece may be connected to the opening of the fluid storage tube by threads, interference fit, fastening, rotatable snap, clip snap or insertion.

Another aspect of the present disclosure is to provide a convenient and sanitary method for collecting urine.

This aspect of the present disclosure is implemented by a solution below.

A convenient and sanitary method for collecting urine, including:

1) preparing a fluid storage tube, a fluid-taking piece and a shielding body, where the fluid storage tube includes an opening and a fluid storage cavity, the fluid-taking piece includes a fluid guiding passage, an air exhaust passage, an annular side wall and a spacer, and the spacer is located in the annular side and configured to separate the fluid guiding passage from the air exhaust passage, the fluid guiding passage has one end as a liquid inlet and the other end as a liquid outlet, where the liquid outlet is located at a lower part of the fluid-taking piece; the air exhaust passage has one end as an air outlet and the other end as an air exhaust opening, and the air exhaust opening is located at the lower part of the fluid-taking piece, a lower part of the fluid-taking piece matches with an opening of the fluid storage tube; the shielding body matches with the fluid-taking piece or is formed in one piece with the fluid-taking piece; and the shielding body is located outside of the fluid storage tube, and a shielding side wall of the shielding body surrounds the fluid storage tube at an angle equal to or less than 360°.

2) aligning the fluid-taking piece with an outlet where fluid leaks, to collect urine; and 3) pouring excessive urine in the fluid-taking piece after the fluid collecting process is completed, and separating the fluid-taking piece from the fluid storage tube, where the shielding body is removed along with the fluid-taking piece, and the fluid storage tube filled with urine is left.

A plug part may be further employed to match with the opening to isolate the urine in the fluid storage tube from the outside.

In the fluid collecting process of the present disclosure, the step of transferring the urine from the urine accommodating cup to the fluid storage tube or test tube is avoided, and the cleanness of the fluid storage tube is ensured and the fluid storage tube containing the urine can be directly used for testing by urine analyzer and test paper after the urine collecting process is completed, thereby improving working efficiency.

The present disclosure is advantageous for sanitation. It is ensured that, after the fluid-taking piece and the shielding body are removed after the fluid collecting process is completed, the outer wall of the fluid storage tube remains clean without being stained, and the fluid storage tube can be directly used for testing by the urine analyzer and test paper.

BRIEF DESCRIPTION OF THE DRAWINGS

FIG. 3 schematically shows that internal threads are provided at an inner side of an opening of the fluid storage tube according to an embodiment of the present disclosure.

FIG. 4 schematically shows that internal threads are provided at an inner side of an opening of the fluid storage tube, the plug part is integrally connected to the outer wall of the fluid storage tube, and longitudinal ribs are provided on the outer wall of the lower part of the fluid storage tube, according to an embodiment of the present disclosure.

FIG. 5 schematically shows that internal threads are provided at an inner side of an opening of the fluid storage tube, the plug part is integrally connected to the outer wall of the fluid storage tube, and protrusions are provided on the outer wall of the lower part of the fluid storage tube, according to an embodiment of the present disclosure.

FIG. 6 schematically shows the cross-section of the lower part of the fluid storage tube according to an embodiment of the present disclosure.

FIG. 7 is a first schematic diagram showing a portion A where the lower part of the fluid connecting piece matches with an opening of the fluid storage tube according to an embodiment of the present disclosure.

FIG. 8 is a second schematic diagram showing a portion A where the lower part of the fluid connecting piece matches with an opening of the fluid storage tube according to an embodiment of the present disclosure.

FIG. 9 is a third schematic diagram showing a portion A where the lower part of the fluid connecting piece matches with an opening of the fluid storage tube according to an embodiment of the present disclosure.

FIG. 10 is a fourth schematic diagram showing a portion A where the lower part of the fluid connecting piece matches with an opening of the fluid storage tube according to an embodiment of the present disclosure.

FIG. 11 schematically shows a fluid-taking piece and a shielding body which are formed in one piece, where the shielding body has a tubular shape, the fluid storage tube and the plug part are formed in one piece, protrusions are provided on the outer wall of the lower part of the fluid storage tube, and the fluid-taking piece is threadedly connected with the fluid storage tube, according to an embodiment of the present disclosure.

FIG. 26 schematically shows the fluid storage tube and the plug part which are formed in one piece according to an embodiment of the present disclosure.

FIG. 27 schematically shows the fluid-taking piece and the shielding body which are fixedly connected according to an embodiment of the present disclosure.

FIG. 28 is a schematic view showing a first example of the body fluid retention device according to an embodiment of the present disclosure.

FIG. 29 schematically shows threads provided at the upper end of the tubular shielding body according to an embodiment of the present disclosure.

LIST OF REFERENCE NUMERALS

Figure 1:
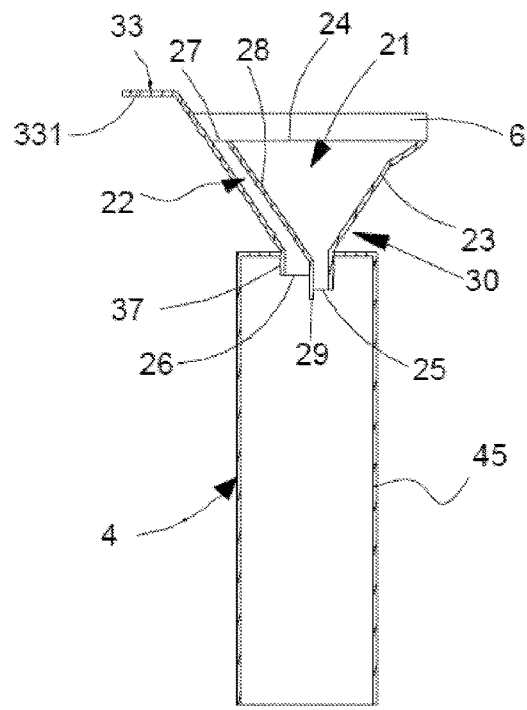
FIG. 1 schematically shows a fluid-taking piece and a shielding body which are formed in one piece, where the shielding body has a tubular shape, according to an embodiment of the present disclosure.

1: Fluid storage tube
   11: Opening; 12: Fluid storage cavity; 13: Lower part of fluid storage tube;
   14: Internal thread; 16: Rib; 17: Protrusion;
2: Fluid-taking piece
   21: Fluid guiding passage; 22: Air exhaust passage; 23: Annular side wall;
   24: Liquid inlet; 25: Liquid outlet; 26: Air exhaust opening;
   27: Air outlet; 28: Spacer; 29: Spacer extension;
   30: Lower part of fluid-taking piece; 31: External thread; 32: Annular step;
   321: First side face; 322: Second side face; 323: Step surface;
   33: Handle; 331: Holding portion; 35: Annular groove;
   351: Bottom of annular groove; 36: Lower end face; 37: External thread;
4: Shielding body;
   43: Bottom plate; 44: Handle; 45: Shielding side wall; 46: Internal thread;
5: Plug part;
6: Fluid collecting plate;
7: Connector;
   70: Through hole; 71: Annular step; 72: Lower end face; 73: External thread;
   74: Internal thread; 75: First annular side wall; 76: Second annular side wall;
   77: Step surface;
8: Sealing ring;
R1: Width of annular groove.

DETAILED DESCRIPTION OF THE EMBODIMENT

The present disclosure will be further illustrated in detail below in conjunction with some embodiments. It may be understood that the described embodiments are merely illustrative without limiting the present disclosure. Accordingly, various modifications and equivalents thereof are intended to be included in the scope of the present disclosure.

First Embodiment

The present disclosure will be further described below in combination with FIGS. 1 to 14.

A disposable sealed body fluid retention device includes a fluid storage tube 1, a fluid-taking piece 2, a shielding body 4, a plug part 5, and a fluid collecting plate 6.

The fluid storage tube 1 in the present embodiment has a structure described below.

As shown in FIG. 3, the fluid storage tube 1 includes an opening 11 and a fluid storage cavity 12, and internal threads 14 are provided at the inner wall of the opening 11 of the fluid storage tube 1.

As shown in FIG. 4, the fluid storage tube 1 includes an opening 11 and a fluid storage cavity 12, and internal threads 14 are provided at the inner wall of the opening 11 of the fluid storage tube 1. A plug part 5 is connected to the outer wall of the fluid storage tube 1, and may be formed in one piece with the fluid storage tube 1. Six longitudinal ribs 6 are arranged on the outer wall of the lower part 13 of the fluid storage tube 1. Alternatively, as shown in FIG. 6, eight longitudinal ribs 6 may be illustratively arranged on the outer wall of the lower part 13 of the fluid storage tube 1.

As shown in FIG. 5, the fluid storage tube 1 includes an opening 11 and a fluid storage cavity 12, and internal threads 14 are provided at the inner wall of the opening 11 of the fluid storage tube 1. A plug part 5 is connected to the outer wall of the fluid storage tube 1, and may be formed in one piece with the fluid storage tube 1. A plurality of protrusions 7 are arranged on the outer wall of the lower part 13 of the fluid storage tube 1.

The lower part 13 of the fluid storage tube 1 may have a cross section of a polygonal shape, for example, a pentagonal, hexagonal or octagonal shape. Alternatively, the fluid storage tube 1 may have a cross section of a polygonal shape, for example, a hexagonal or octagonal shape.

The provision of the skidproof structure, such as the ribs, protrusions, skidproof patterns and coarse surfaces, on the lower part 30 of the liquid storage tube is advantageous for easy holding of the liquid storage tube 1 being separated from the fluid-taking piece 2 after the fluid taking process has completed and for easy applying of forces to separate the fluid-taking piece 2 from the liquid storage tube 1.

The plug part 5 in the embodiment may be embodied as follows.

Figure 2:
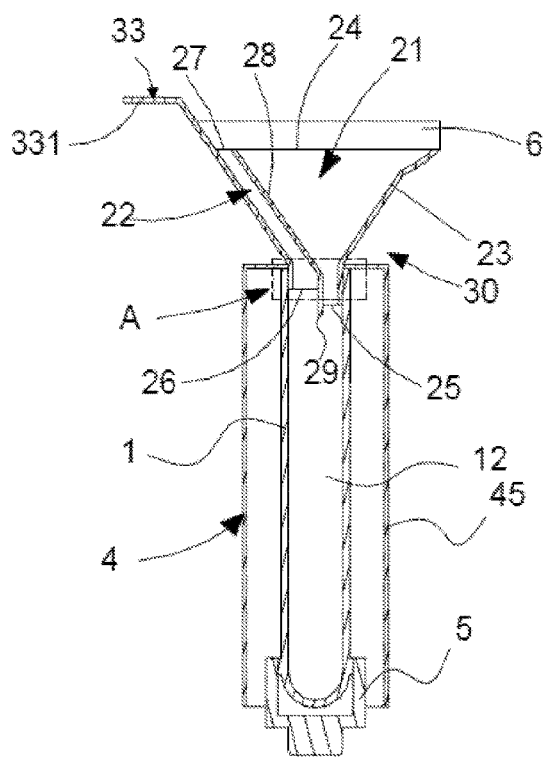
FIG. 2 schematically shows a fluid-taking piece and a shielding body which are formed in one piece, where the shielding body has a tubular shape, a plug part is provided at the lower end of the fluid storage tube, and the fluid-taking piece is threadedly connected with the fluid storage tube, according to an embodiment of the present disclosure.
Figure 14:
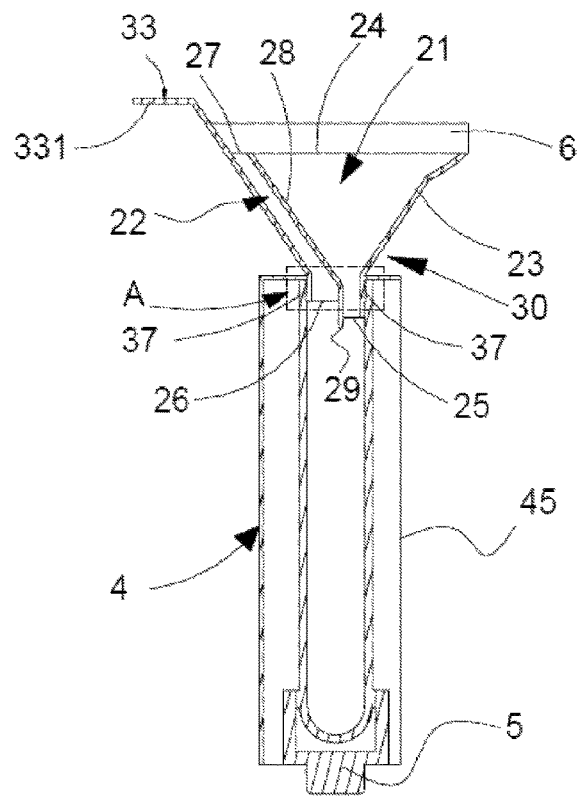
FIG. 14 schematically shows a fluid-taking piece and a shielding body which are formed in one piece, where the shielding body is C-shaped, internal threads are provided at an inner side of an opening of the fluid storage tube, a plug part is provided at the lower end of the fluid storage tube, and the fluid-taking piece is threadedly connected with the fluid storage tube, according to an embodiment of the present disclosure.

As shown in FIGS. 2 and 14, the lower part 13 of the fluid storage tube is inserted into the plug part 5.

As shown in FIGS. 4, 5, 11 and 13, the plug part 5 is connected to the outer wall of the fluid storage tube 1 and preferably formed in one piece with the fluid storage tube 1.

The fluid-taking piece 2 in the embodiment may have the structure described below.

Figure 12:
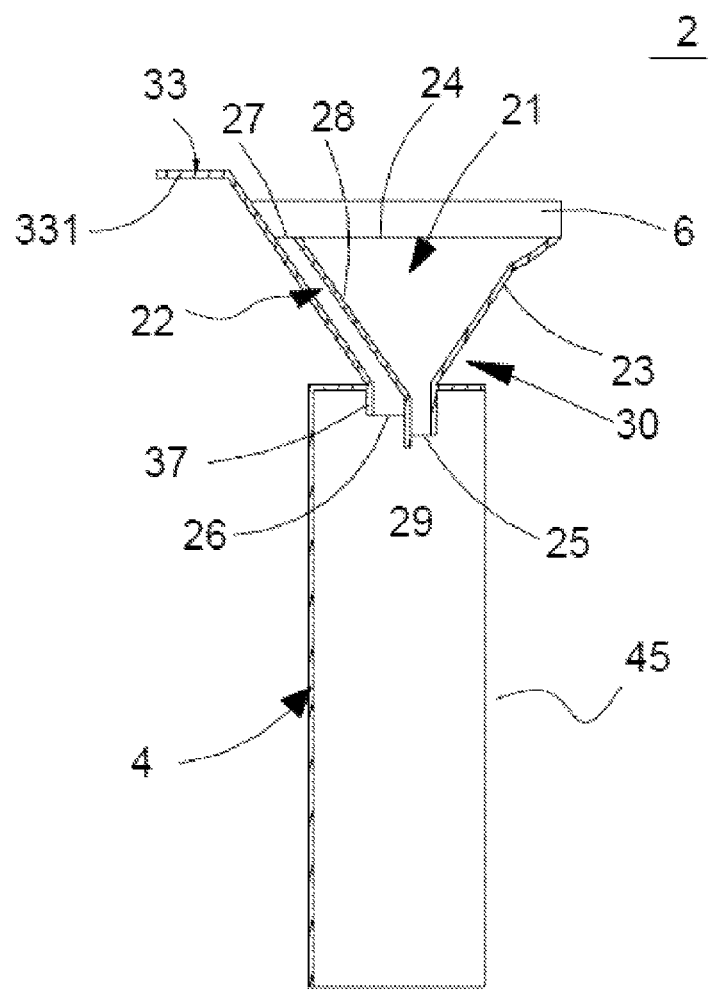
FIG. 12 schematically shows a fluid-taking piece and a shielding body which are formed in one piece, where the shielding body is C-shaped, according to an embodiment of the present disclosure.
Figure 13:
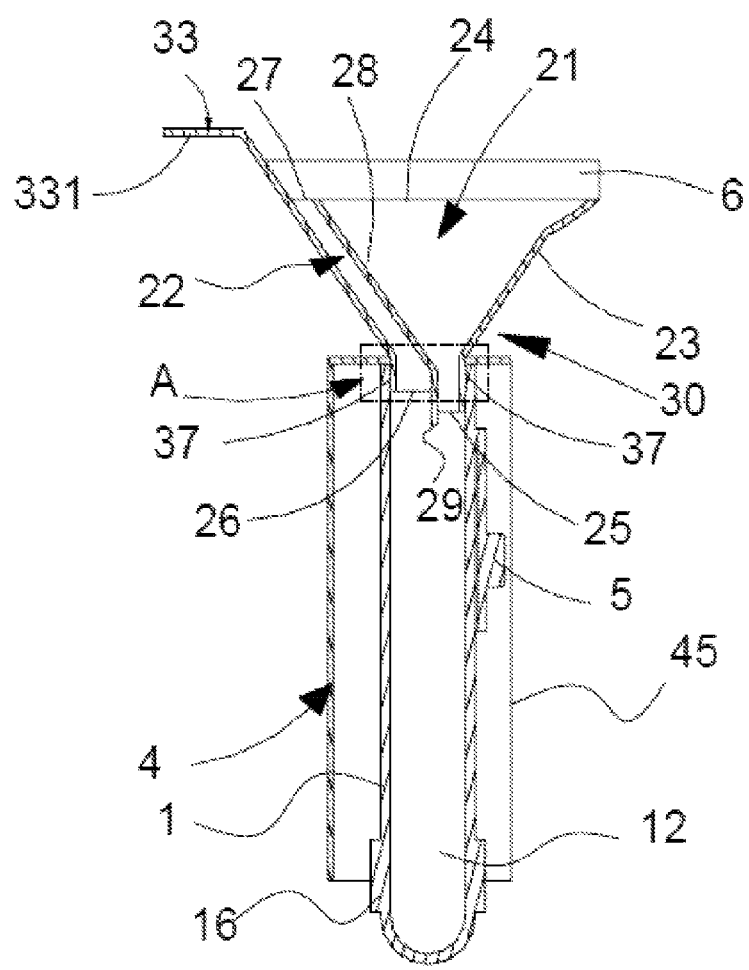
FIG. 13 schematically shows a fluid-taking piece and a shielding body which are formed in one piece, where the shielding body is C-shaped, the fluid storage tube and the plug part are formed in one piece, longitudinal ribs are provided on the outer wall of the lower part of the fluid storage tube, and the fluid-taking piece is threadedly connected with the fluid storage tube, according to an embodiment of the present disclosure.

As shown in FIG. 1, the fluid-taking piece 2 includes a fluid guiding passage 21, an air exhaust passage 22, a spacer 28, an annular side wall 23 and a handle 33. The fluid guiding passage 21 and the air exhaust passage 22 are separated from each other by the spacer 28 within the annular side wall 23. The fluid guiding passage 21 has one end as a liquid inlet 24 and the other end as a liquid outlet 25, the air exhaust passage 22 has one end as an air outlet 27 and the other end as an air exhaust opening 26, and the air exhaust opening 26 and the liquid outlet 25 are at different planes and preferably the air exhaust opening 26 is at a higher level than the liquid outlet 25. A holding portion 331 of the handle 33 is disposed higher than the top of the annular side wall 23. A liquid collecting plate 6, which is used for collecting urine into the fluid guiding passage to avoid spurting of the urine to outside of the fluid-taking piece 2, is fixed to the top of the annular side wall 23 of the fluid-taking piece 2. The liquid collecting plate 6 may be arranged at both sides of the handle 33, or at either side of the handle 33. Alternatively, the liquid collecting plate 6 may be omitted. An anti-spurting layer may be disposed on the fluid guiding passage 21 of the fluid-taking piece 2 to suppress the spurting of urine in the fluid-taking process. A spacer extension 29, which is extended downwards from the spacer 28, is arranged between the air exhaust opening 26 and the liquid outlet 25 to prevent liquid from entering into the air exhaust opening 26. Threads 37 are provided on the outer wall of the lower part of the fluid-taking piece. A shielding side wall 45 of the shielding body 4 may be formed in one piece with the fluid-taking piece 2, and may have a tubular shape surrounding the fluid storage tube at an angle of 360°. The shielding body 4 is posited at the outside of the fluid storage tube 1, and the bottom of the fluid storage tube 1 is lower than the lowest portion of the shielding body 4. As shown in FIG. 12, the shielding side wall 45 of the shielding body 4 is formed in one piece with the lower part 30 of the fluid-taking piece and has a C-shape (i.e. a sector shape) surrounding the fluid storage tube at an angle of 340°, and the shielding body 4 is positioned at the outside of the fluid storage tube 1.

In the present embodiment, the liquid collecting plate 6 is fixed to the fluid-taking piece 2 by the way described below.

The liquid collecting plate 6 is fixed to the top of the annular side wall 23 of the fluid-taking piece 2, and is used for collecting urine into the fluid guiding passage to avoid spurting of the urine onto the fluid-taking piece 2. The liquid collecting plate 6 may be arranged at both sides of the handle 33, or at either side of the handle 33. Alternatively, the liquid collecting plate 6 may be omitted.

An anti-spurting layer may be disposed on the fluid guiding passage of the fluid-taking piece 2 to absorb the impact by the urine in the fluid-taking process, thereby eliminating urine spurted to the outside of the fluid-taking piece 2.

The lower part 30 of the fluid-taking piece is fixed to the opening 11 of the fluid storage tube 1 by the way described below.

As shown in FIG. 2, the lower part 30 of the fluid-taking piece is detachably and sealedly connected to the opening 11 of the fluid storage tube 1, that is, the external threads 37 on the lower part 30 of the fluid-taking piece match with the internal threads 14 on the inner wall of the opening 11 of the fluid storage tube 1.

Alternatively, the lower part 30 of the fluid-taking piece may be insertedly connected to the opening 11 of the fluid storage tube 1.

As shown in FIG. 7, a sealing ring 8 is arranged at the opening 11 of the fluid storage tube 1, where the external threads 73 are provided on the outer wall of the lower part 30 of the fluid-taking piece, the internal threads 14 are provided on the inner wall of the opening of the fluid storage tube 1, and the sealing ring 8 is arranged between the opening 11 of the fluid storage tube 1 and the lower part 30 of the fluid-taking piece.

As shown in FIG. 8, a sealing ring 8 is arranged at the opening 11 of the fluid storage tube 1, where the external threads 73 are provided on the outer wall of the lower part 30 of the fluid-taking piece, and the sealing ring 8 is arranged between the opening 11 of the fluid storage tube 1 and the lower part 30 of the fluid-taking piece.

As shown in FIG. 9, a sealing ring 8 is arranged at the opening 11 of the fluid storage tube 1, where the sealing ring 8 is arranged between the opening 11 of the fluid storage tube 1 and the lower part 30 of the fluid-taking piece. Alternatively, the opening 11 of the fluid storage tube 1 may be insertedly connected to the lower part 30 of the fluid-taking piece, without a sealing ring between the opening of the fluid storage tube 1 and the lower part of the fluid-taking piece.

As shown in FIG. 10, a sealing ring 8 is arranged at the opening 11 of the fluid storage tube 1, the internal threads 14 are provided on the inner wall of the opening of the fluid storage tube 1, and the sealing ring 8 is arranged between the opening 11 of the fluid storage tube 1 and the lower part 30 of the fluid-taking piece.

As shown in FIGS. 7 to 10, the sealing ring may be made of elastic material, and is used for not only easy inserting thereof but also a sealing effect.

Alternatively, the lower part 30 of the fluid-taking piece may be insertedly connected to the opening 11 of the fluid storage tube 1 directly without the sealing ring 8.

To collect the urine, the fluid-taking piece 2 is aligned with an outlet where fluid such as urine leaks. After the liquid collecting process is completed, excessive fluid in the fluid-taking piece 2 is poured. Subsequently, the handle 33 is held by one hand while the plug part 5 disposed at the lower part 13 of the fluid storage tube is held by the other hand, so that the fluid storage tube 1 may be removed from the fluid-taking piece 2. At this time, the fluid-taking piece 2 and the shielding body 4 may be disposed, and the plug part 5 attached to the lower part 13 of the fluid storage tube 1 is taken off and mounted at the opening 11 of the fluid storage tube 1 so that the fluid storage cavity 12 of the fluid storage tube 1 is isolated from the outside.

In the present embodiment, the fluid-taking piece 2 and the shielding body 4 may be manufactured separately, and subsequently assembled fixedly or in interference with each other. Alternatively, the fluid-taking piece 2 and the shielding body 4 may be connected to each other by threads, rotatable snap or magnetic adsorption. The shielding body 4 may be manufactured by elastic material, and the opening of the shielding body 4 is connected to the outer wall of the fluid storage tube 1 or the lower part 30 of the fluid-taking piece by elastic hoop fit or in interference fit with each other. In use, the shielding body 4 may be directly inserted on the outer wall of the fluid storage tube 1 or the lower part 30 of the fluid-taking piece, and may be directly disposed after the urine taking process is completed. The shielding body 4 may be connected to the fluid storage tube 1 or the fluid-taking piece 2 in various ways which are not limited herein.

Second Embodiment

The present disclosure will be further described in detail below in conjunction with FIGS. 26, 28, 3, 29, 30, 32 and 31.

A disposable sealed body fluid retention device includes a fluid storage tube 1, a fluid-taking piece 2, a shielding body 4, a plug part 5, and a fluid collecting plate 6.

The fluid storage tube 1 includes an opening 11 and a fluid storage cavity 12, and internal threads 14 are provided at the inner wall of the opening 11 of the fluid storage tube 1. The plug part 5 is mounted to the lower part 13 of the fluid storage tube.

The fluid-taking piece 2 includes a fluid guiding passage 21, an air exhaust passage 22, a spacer 28, an annular side wall 23 and a handle 33. A holding portion 331 of the handle 33 is arranged higher than the top of the annular side wall 23. The fluid guiding passage 21 and the air exhaust passage 22 are separated from each other by the spacer 28 within the annular side wall 23. The fluid guiding passage 21 has one end as a liquid inlet 24 and the other end as a liquid outlet 25, and the liquid outlet 25 is located at the lower end face of the lower part 30 of the fluid-taking piece. The air exhaust passage 22 has one end as an air outlet 27 and the other end as an air exhaust opening 26, and the air exhaust opening 26 is located at the lower end face of the lower part 30 of the fluid-taking piece. The air exhaust opening 26 and the liquid outlet 25 may be at the same plane, and a spacer extension 29, which is extended downwards from the spacer 28, is arranged between the air exhaust opening 26 and the liquid outlet 25 to prevent liquid from entering into the air exhaust opening 26.

The liquid collecting plate 6 is fixed to the top of the annular side wall 23 of the fluid-taking piece 2, and is used for collecting urine into the fluid guiding passage to avoid spurting of the urine onto the fluid-taking piece 2. The liquid collecting plate 6 may be arranged at both sides of the handle 33, or at either side of the handle 33. Alternatively, the liquid collecting plate 6 may be omitted. The holding portion 331 of the handle 33 of the fluid-taking piece 2 is arranged higher than the top end face of the liquid collecting plate 6, and an anti-spurting layer may be disposed on the fluid guiding passage of the fluid-taking piece 2 to suppress the spurting of urine in the fluid-taking process.

An annular step 32 is provided at the outer wall of the lower part 30 of the fluid-taking piece, and includes a first side face 321, a second side face 322 and a step surface 323 which is connected to both the first and second side faces 321 and 322. The second side face is adjacent to the lower end face 36. External threads 31 are provided on the first side face 321 while external threads 37 are provided on the second side face 322.

The lower part 30 of the fluid-taking piece is threadedly connected with the opening 11 of the fluid storage tube 1. Specifically, the external threads 37 on the second side face 322 at the lower part 30 of the fluid-taking piece match with the internal threads 14 on the inner wall of the opening 11 of the fluid storage tube 1.

The shielding body 4 has a tubular shape surrounding the fluid storage tube at an angle of 360°, and is posited at the outside of the fluid storage tube 1. Internal threads 46 are provided on the inner wall at the upper part of the shielding body 4, so that the shielding body 4 may be threadedly connected with the lower part 30 of the fluid-taking piece, specifically the internal threads 46 in the shielding body 4 match with the external threads 31 on the first side face 321 at the lower part 30 of the fluid-taking piece. The shielding body 4 includes a handle 44. The fluid-taking piece 2 may be alternatively connected with the shielding body 4 by way of rotatable snap, interference fit, fastening, clip snap or magnetic adsorption, which is not limited herein.

To collect the urine, the fluid-taking piece 2 is aligned with an outlet where fluid such as urine leaks. After the liquid collecting process is completed, excessive fluid in the fluid-taking piece 2 is poured. Subsequently, the handle 33 is held by one hand while the plug part 5 disposed at the lower part of the fluid storage tube is held by the other hand, so that the fluid storage tube 1 may be removed from the fluid-taking piece 2. At this time, the fluid-taking piece 2 and the shielding body 4 may be disposed, and the plug part 5 is mounted at the opening 11 of the fluid storage tube 1 so that the fluid storage cavity 12 of the fluid storage tube 1 is isolated from the outside. In the present embodiment, the fluid storage tube 1 may alternatively have a structure as shown in FIG. 26, and the plug part 5 may be formed in one piece with the fluid storage tube 1. After the liquid collecting process is completed, it is very convenience to mount the plug part 5 onto the opening 11.

Third Embodiment

The present disclosure will be further described in detail below in conjunction with FIGS. 26, 3, 30, 32 and 31.

A disposable sealed body fluid retention device includes a fluid storage tube 1, a fluid-taking piece 2, a shielding body 4, a plug part 5, and a fluid collecting plate 6.

The fluid storage tube 1 includes an opening 11 and a fluid storage cavity 12, and internal threads 14 are provided at the inner wall of the opening 11 of the fluid storage tube 1. The plug part 5 is formed in one piece with the fluid storage tube.

The fluid-taking piece 2 includes a fluid guiding passage 21, an air exhaust passage 22, a spacer 28, an annular side wall 23 and a handle 33. A holding portion 331 of the handle 33 is arranged higher than the top of the annular side wall 23. The fluid guiding passage 21 and the air exhaust passage 22 are separated from each other by the spacer 28 within the annular side wall 23. The fluid guiding passage 21 has one end as a liquid inlet 24 and the other end as a liquid outlet 25, and the liquid outlet 25 is located at the lower end face of the lower part 30 of the fluid-taking piece. The air exhaust passage 22 has one end as an air outlet 27 and the other end as an air exhaust opening 26, and the air exhaust opening 26 is located at the lower end face of the lower part 30 of the fluid-taking piece. The air exhaust opening 26 and the liquid outlet 25 may be at the same plane, and a spacer extension 29, which is extended downwards from the spacer 28, is arranged between the air exhaust opening 26 and the liquid outlet 25 to prevent liquid from entering into the air exhaust opening 26.

The liquid collecting plate 6 is fixed to the top of the annular side wall 23 of the fluid-taking piece 2, and is used for collecting urine into the fluid guiding passage to avoid spurting of the urine onto the fluid-taking piece 2. The liquid collecting plate 6 may be arranged at both sides of the handle 33, or at either side of the handle 33. Alternatively, the liquid collecting plate 6 may be omitted. The holding portion 331 of the handle 33 of the fluid-taking piece 2 is arranged higher than the top end face of the liquid collecting plate 6, and an anti-spurting layer may be disposed on the fluid guiding passage of the fluid-taking piece 2 to suppress the spurting of urine in the fluid-taking process.

An annular step 32 is provided at the outer wall of the lower part 30 of the fluid-taking piece, and includes a first side face 321, a second side face 322 and a step surface 323 which is connected to both the first and second side faces 321 and 322. The second side face is adjacent to the lower end face 36. External threads 31 are provided on the first side face 321 while external threads 37 are provided on the second side face 322.

The lower part 30 of the fluid-taking piece is threadedly connected with the opening 11 of the fluid storage tube 1. Specifically, the external threads 37 on the second side face 322 at the lower part 30 of the fluid-taking piece match with the internal threads 14 on the inner wall of the opening 11 of the fluid storage tube 1.

The shielding side wall 45 of the shielding body 4 surrounds the fluid storage tube at an angle of 360°, a bottom plate 43 which may be formed in one piece with the shielding side wall 45 is provided to the bottom of the shielding side wall 45. The shielding body 4 has a cylindrical shape and further includes a handle 44. At the opening of the shielding body 4, internal threads 46 are provided on the inner side of the shielding side wall 45.

The shielding body 4 is detachably fixed to the lower part 30 of the fluid-taking piece by way of threads, rotatable snap, etc. When the shielding body 4 is fixed to the lower part 30 of the fluid-taking piece, the internal threads 46 on the inner side of the shielding side wall 45 of the shielding body 4 match with the external threads 31 on the first side wall 321 at the lower part 30 of the fluid-taking piece.

The fluid-taking piece 2 may be alternatively connected with the shielding body 4 by way of rotatable snap, interference fit, fastening, clip snap or magnetic adsorption. The shielding body 4 may be manufactured by elastic material, and the opening of the shielding body 4 is connected to the outer wall of the fluid storage tube 1 or the lower part 30 of the fluid-taking piece by elastic hoop fit or in interference fit with each other. In use, the shielding body 4 may be directly inserted on the outer wall of the fluid storage tube 1 or the lower part 30 of the fluid-taking piece, and may be directly disposed after the urine taking process is completed. The shielding body 4 may be connected to the fluid storage tube 1 or the fluid-taking piece 2 in various ways which are not limited herein.

To collect the urine, the fluid-taking piece 2 is aligned with an outlet where fluid such as urine leaks. After the liquid collecting process is completed, excessive fluid in the fluid-taking piece 2 is poured. Subsequently, the handle 33 is held by one hand while the handle 44 of the shielding body 4 is held by the other hand, so that the shielding body 4 may be removed and disposed. Then, the fluid storage tube 1 is held by hand and the fluid-taking piece 2 is removed and disposed. Subsequently, the plug part 5 is mounted at the opening 11 of the fluid storage tube 1 so that the fluid storage cavity 12 of the fluid storage tube 1 is isolated from the outside.

Fourth Embodiment

The present disclosure will be further described in detail below in conjunction with FIGS. 32, 33, 34 and 35.

A disposable sealed body fluid retention device includes a fluid storage tube 1, a fluid-taking piece 2, a shielding body 4, a plug part 5, and a fluid collecting plate 6.

The fluid storage tube 1 includes an opening 11 and a fluid storage cavity 12, and the plug part 5 is arranged on the lower part 30 of the fluid storage tube.

The fluid-taking piece 2 includes a fluid guiding passage 21, an air exhaust passage 22, a spacer 28, an annular side wall 23 and a handle 33. A holding portion 331 of the handle 33 is arranged higher than the top of the annular side wall 23. The fluid guiding passage 21 and the air exhaust passage 22 are separated from each other by the spacer 28 within the annular side wall 23. The fluid guiding passage 21 has one end as a liquid inlet 24 and the other end as a liquid outlet 25, and the liquid outlet 25 is located at the lower end face 36 of the lower part 30 of the fluid-taking piece. The air exhaust passage 22 has one end as an air outlet 27 and the other end as an air exhaust opening 26, and the air exhaust opening 26 is located at the lower end face 36 of the lower part 30 of the fluid-taking piece. The air exhaust opening 26 and the liquid outlet 25 are located on the lower end face 36, and a spacer extension 29, which is extended downwards from the spacer 28, is arranged between the air exhaust opening 26 and the liquid outlet 25 to prevent liquid from entering into the air exhaust opening 26.

The liquid collecting plate 6 is fixed to the top of the annular side wall 23 of the fluid-taking piece 2, and is used for collecting urine into the fluid guiding passage to avoid spurting of the urine onto the fluid-taking piece 2. The liquid collecting plate 6 may be arranged at both sides of the handle 33, or at either side of the handle 33. Alternatively, the liquid collecting plate 6 may be omitted. The holding portion 331 of the handle 33 of the fluid-taking piece 2 is arranged higher than the top end face of the liquid collecting plate 6, and an anti-spurting layer may be disposed on the fluid guiding passage of the fluid-taking piece 2 to suppress the spurting of urine in the fluid-taking process.

An annular step 32 is provided at the lower part 30 of the fluid-taking piece, and includes a first side face 321, a second side face 322 and a step surface 323 which is connected to both the first and second side faces 321 and 322. The second side face is adjacent to the lower end face 36. External threads 31 are provided on the first side face 321.

A sealing ring 8 is arranged at the opening 11 of the fluid storage tube 1, and functions to enclose the outer and inner walls and the top edge of the opening of the fluid storage tube. The sealing ring 8 may be made of elastic material.

The lower part 30 of the fluid-taking piece is insertedly connected with the opening 11 of the fluid storage tube 1. Specifically, the sealing ring 8 is arranged between the opening 11 of the fluid storage tube 1 and the lower part 30 of the fluid-taking piece, and is used for sealing and easy inserting/removing of the lower part 30 of the fluid-taking piece to/from the opening 11 of the fluid storage tube 1.

The shielding side wall 45 of the shielding body 4 surrounds the fluid storage tube at an angle of 360°, a bottom plate 43 which is formed in one piece with the shielding side wall 45 is provided to the bottom of the shielding side wall 45. The shielding body 4 has a cylindrical shape and further includes a handle 44. At the opening of the shielding body 4, internal threads 46 are provided on the inner side of the shielding side wall 45.

The shielding body 4 is detachably fixed to the lower part 30 of the fluid-taking piece by way of threads, rotatable snap, etc. When the shielding body 4 is fixed to the lower part 30 of the fluid-taking piece, the internal threads 46 on the inner side of the shielding side wall 45 of the shielding body 4 match with the external threads 31 on the first side wall 321 at the lower part 30 of the fluid-taking piece.

The fluid-taking piece 2 may be alternatively connected with the shielding body 4 by way of rotatable snap, interference fit, fastening, clip snap or magnetic adsorption, which is not limited herein.

To collect the urine, the fluid-taking piece 2 is aligned with an outlet where fluid such as urine leaks. After the liquid collecting process is completed, excessive fluid in the fluid-taking piece 2 is poured. Subsequently, the handle 33 is held by one hand while the handle 44 of the shielding body 4 is held by the other hand, so that the shielding body 4 may be removed and disposed. Then, the fluid storage tube 1 is held by hand and the fluid-taking piece 2 is removed and disposed. Subsequently, the plug part 5 is mounted at the opening 11 of the fluid storage tube 1 so that the fluid storage cavity 12 of the fluid storage tube 1 is isolated from the outside.

The fluid storage tube 1 may also have the structure as shown in FIG. 26, and the plug part 5 is formed in one piece with the fluid storage tube 1.

Fifth Embodiment

Figure 36:
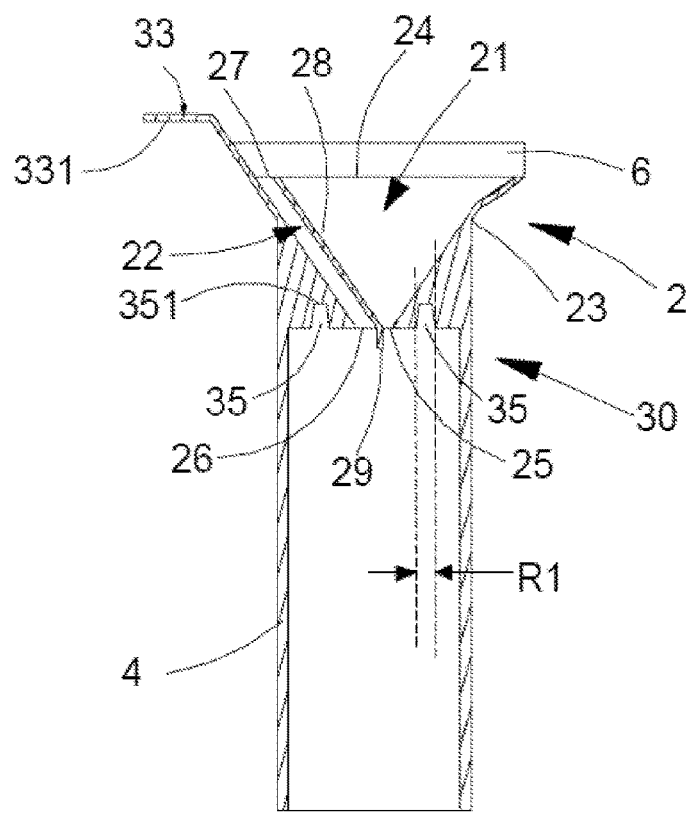
FIG. 36 schematically shows that the fluid-taking piece and the shielding body are formed in one piece and an annular groove is provided at the lower end face of the fluid-taking piece, according to an embodiment of the present disclosure.
Figure 37:
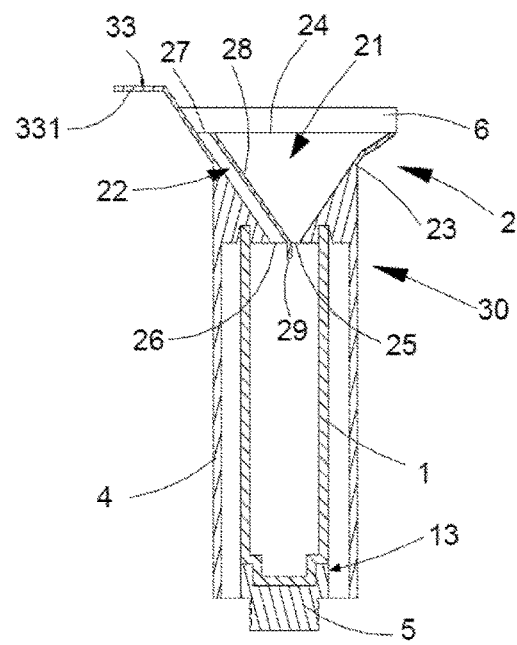
FIG. 37 is a schematic view showing a second example of the body fluid retention device according to an embodiment of the present disclosure.
Figure 38:
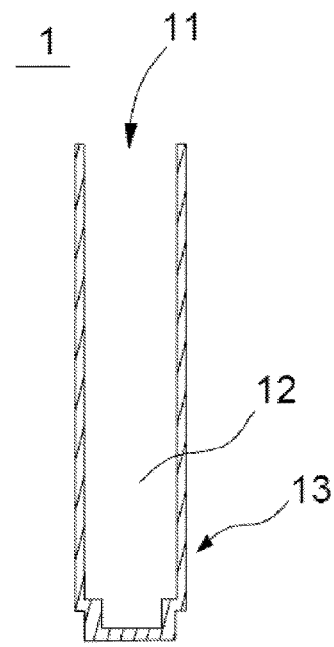
FIG. 38 is a first schematic view showing the fluid storage tube according to an embodiment of the present disclosure.
Figure 39:
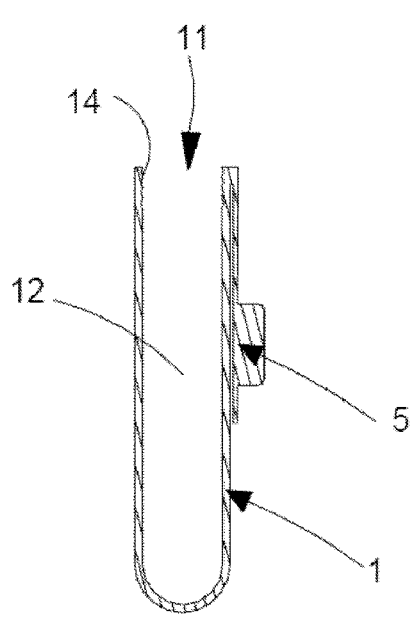
FIG. 39 schematically shows that the fluid storage tube and the plug part are formed in one piece and internal threads are provided at the inner side of the opening of the fluid storage tube, according to an embodiment of the present disclosure.

The present disclosure will be further described in detail below in conjunction with FIGS. 36, 37 and 38.

A disposable sealed body fluid retention device includes a fluid storage tube 1, a fluid-taking piece 2, a shielding body 4, and a plug part 5.

The fluid storage tube 1 includes an opening 11 and a fluid storage cavity 12, and the plug part 5 is arranged on the lower part 30 of the fluid storage tube.

The fluid-taking piece 2 includes a fluid guiding passage 21, an air exhaust passage 22, a spacer 28, an annular side wall 23 and a handle 33. A holding portion 331 of the handle 33 is arranged higher than the top of the annular side wall 23. The fluid guiding passage 21 and the air exhaust passage 22 are separated from each other by the spacer 28 within the annular side wall 23. The fluid guiding passage 21 has one end as a liquid inlet 24 and the other end as a liquid outlet 25, and the liquid outlet 25 is located at the lower end face 36 of the lower part 30 of the fluid-taking piece. The air exhaust passage 22 has one end as an air outlet 27 and the other end as an air exhaust opening 26, and the air exhaust opening 26 is located at the lower end face 36 of the lower part 30 of the fluid-taking piece. The air exhaust opening 26 and the liquid outlet 25 are located on the lower end face 36, and a spacer extension 29, which is extended downwards from the spacer 28, is arranged between the air exhaust opening 26 and the liquid outlet 25 to prevent liquid from entering into the air exhaust opening 26.

The liquid collecting plate 6 is fixed to the top of the annular side wall 23 of the fluid-taking piece 2, and is used for collecting urine into the fluid guiding passage to avoid spurting of the urine onto the fluid-taking piece 2. The liquid collecting plate 6 may be arranged at both sides of the handle 33, or at either side of the handle 33. Alternatively, the liquid collecting plate 6 may be omitted. The holding portion 331 of the handle 33 of the fluid-taking piece 2 is arranged higher than the top end face of the liquid collecting plate 6, and an anti-spurting layer may be disposed on the fluid guiding passage of the fluid-taking piece 2 to suppress the spurting of urine in the fluid-taking process.

An annular groove 35 is provided at the lower end face 36 of the lower part 30 of the fluid-taking piece, and the width R1 of the annular groove 35 is gradually reduced in a direction from the lower end face 36 to the bottom of the annular groove 35 to facilitate the insertion by the opening 11 of the fluid storage tube 1. Thus, the opening of the fluid storage tube 1 may be placed in the annular groove 35, and the lower part 30 of the fluid-taking piece is sealedly connected to the opening 11 of the fluid storage tube 1.

The shielding body 4 is located below the fluid-taking piece and may be formed in one piece with the fluid-taking piece 2. The shielding side wall 45 of the shielding body 4 has a tubular shape that surrounds the fluid storage tube at an angle of 360°. The fluid-taking piece 2 may be alternatively connected with the shielding body 4 by way of threads, rotatable snap, clip snap or magnetic adsorption.

To collect the urine, the fluid-taking piece 2 is aligned with an outlet where fluid such as urine leaks. After the liquid collecting process is completed, excessive fluid in the fluid-taking piece 2 is poured. Subsequently, the plug part 5 at the lower part 13 of the fluid storage tube is held by hand, the shielding body 4 is removed while the fluid-taking piece 2 is removed because the shielding body 4 is fixedly connected to the fluid-taking piece 2, and then the plug part 5 is mounted at the opening 11 of the fluid storage tube 1.

Six Embodiment

The present disclosure will be further described in detail below in conjunction with FIGS. 26, 23, 24, 25 and 39.

A disposable sealed body fluid retention device includes a fluid storage tube 1, a fluid-taking piece 2, a shielding body 4, a fluid collecting plate 6, and a connector 7.

The fluid storage tube 1 includes an opening 11 and a fluid storage cavity 12, internal threads 14 are provided at the inner wall of the opening 11 of the fluid storage tube 1, and the plug part 5 is formed in one piece with the fluid storage tube 1.

The connector 7 includes an axial through hole 70, the wall of which is provided with internal threads 74. An annular step 71 is provided along the outer wall of the connector 7 from the lower end face 72 of the connector 7, and includes a first annular side wall 75, a step surface 77 and a second annular side wall 76. The first annular side wall 75 is folded in a direction to the center of the connector 7 to form the step surface 77, the step surface 77 is folded downwards to form the second annular side wall 76, and the second annular side wall 76 is adjacent to the lower end face 72. External threads 73 are formed on the first annular side wall 75 and the second annular side wall 76, respectively. The connector 7 is detachably connected to the opening 11 of the fluid storage tube 1, particularly, the external thread 73 on the second annular side wall 76 match with the internal threads 14 on the inner wall of the opening of the fluid storage tube 1.

The fluid-taking piece 2 includes a fluid guiding passage 21, an air exhaust passage 22, an annular side wall 23 and a handle 33. A holding portion 331 of the handle 33 is arranged higher than the top of the annular side wall 23. The fluid guiding passage 21 and the air exhaust passage 22 are separated from each other by a spacer 28 within the annular side wall 23. The fluid guiding passage 21 has one end as a liquid inlet 24 and the other end as a liquid outlet 25, and the liquid outlet 25 is located at the lower end face 36 of the lower part 30 of the fluid-taking piece. The air exhaust passage 22 has one end as an air outlet 27 and the other end as an air exhaust opening 26, and the air exhaust opening 26 is located at the lower end face 36 of the lower part 30 of the fluid-taking piece. The air exhaust opening 26 and the liquid outlet 25 are located on the same place. External threads 31 are provided at the lower part 30 of the fluid-taking piece, so that the lower part 30 of the fluid-taking piece may be detachably connected to the through hole 70 by for example the matching between the external threads 31 on the lower part 30 of the fluid-taking piece and the internal threads 74 of the through hole 70. Alternatively, the lower part 30 of the fluid-taking piece and the through hole 70 may be fixedly connected in other ways, for example interference fit, fastening, threads in combination with thread adhesive, and so on. Both the air exhaust opening 26 and the liquid outlet 25 are in communication with the through hole 70.

A spacer extension 29, which is extended downwards from the spacer 28 and may be formed in one piece with the fluid-taking piece 2, is arranged between the air exhaust opening 26 and the liquid outlet 25. The lowest portion of the spacer extension 29 is disposed lower than the lowest portions of the air exhaust opening 26 and the liquid outlet 25.

The liquid collecting plate 6 is fixed to the top of the annular side wall 23 of the fluid-taking piece 2, and is used for collecting urine into the fluid guiding passage to avoid spurting of the urine onto the fluid-taking piece 2. An anti-spurting layer may be further disposed on the fluid guiding passage of the fluid-taking piece 2 to suppress the spurting of urine in the fluid-taking process.

The shielding body 4 has a tubular shape and may be provided with or without a handle 44. The fluid storage tube 1 is inserted into the shielding body 4, that is, the shielding body 4 is located outside of the fluid storage tube 1. The shielding body 4 may be fixedly connected with the lower part 30 of the fluid-taking piece by way of threads, rotatable snap, interference fit, or fastening. The lowest portion of the shielding body 4 may be disposed no higher than the lowest portion of the fluid storage tube.

Alternatively, the shielding body 4 may be formed in one piece with the lower part 30 of the fluid-taking piece. When the shielding body 4 has a tubular shape, the lowest portion of the shielding body 4 may be disposed no lower than the lowest portion of the fluid storage tube.

When the shielding body 4 is fixedly connected to the fluid-taking piece 2, after the urine collecting process is completed, the handle 33 is held by one hand and the handle 14 is held by the other hand, so that the shielding body 4 is unthreaded and then the fluid storage tube 1 is unthreaded, and the plug part 5 is mounted at the opening 11 of the fluid storage tube 1 to isolate the fluid storage cavity 12 of the fluid storage tube 1 from the outside. When the shielding body 4 is formed in one piece with the fluid-taking piece 2, the handle 44 of the shielding body 4 may be omitted. In this case, after the fluid taking process is completed, the handle 33 is held by one hand and the bottom of the fluid storage tube 1 is held by the other hand to remove the fluid storage tube 1, and the plug part 5 on the fluid storage tube 1 is mounted at the opening 11 of the fluid storage tube 1 to isolate the fluid storage cavity 12 of the fluid storage tube 1 from the outside. When the shielding body 4 is formed in one piece with the fluid-taking piece 2, the fluid-taking piece 2 and the connector 7 are removed together, and the plug part 5 on the fluid storage tube 1 is mounted at the opening 11 of the fluid storage tube 1 to isolate the fluid storage cavity 12 of the fluid storage tube 1 from the outside.

The connector 7 may be detachably connected with the opening 11 of the fluid storage tube 1 by way of threads, rotatable snap, insertion and so on. Likewise, the lower part 30 of the fluid-taking piece may be detachably connected with the connector 7 by way of threads, rotatable snap, clip snap, magnetic adsorption, fastening, interference fit and so on. Alternatively, the lower part 30 of the fluid-taking piece may be formed in one piece with the connector 7.

Seventh Embodiment

Figure 40:
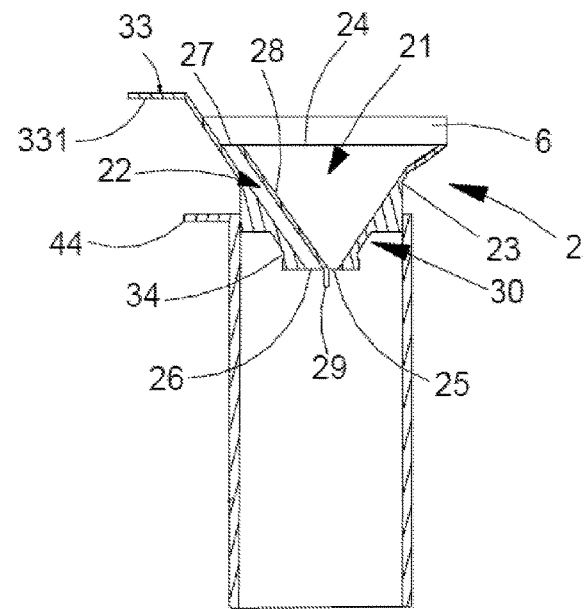
FIG. 40 schematically shows the arrangement of an annular groove at the lower part of the fluid-taking piece and the magnetic attachment between the fluid-taking piece and the shielding body, according to an embodiment of the present disclosure.
Figure 41:
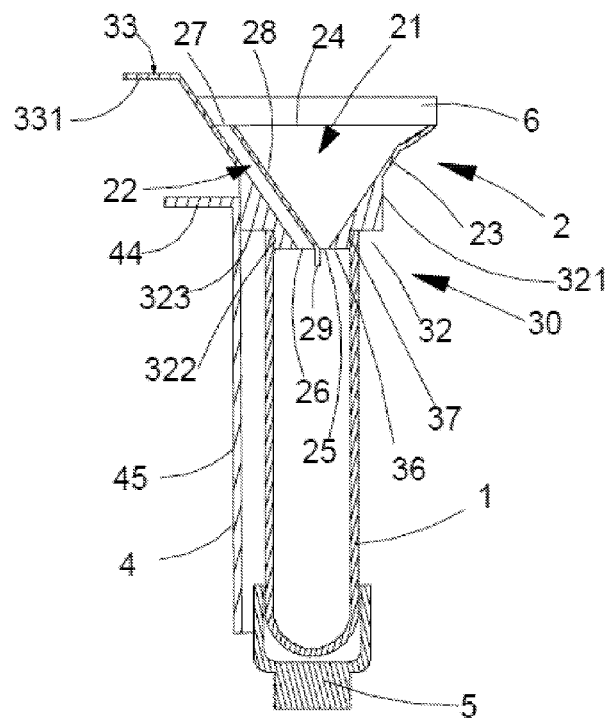
FIG. 41 schematically shows the C-shaped shielding body of the body fluid retention device and the connection between the shielding body and the fluid-taking piece, according to an embodiment of the present disclosure.
Figure 42:
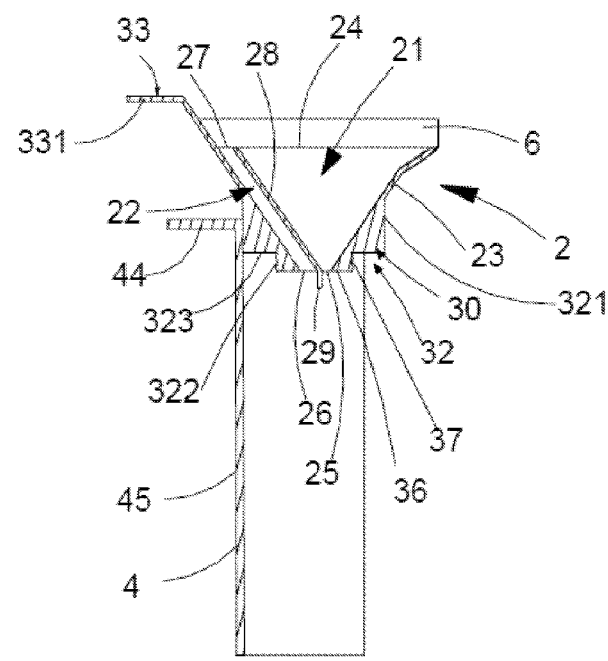
FIG. 42 schematically shows the connection between the shielding body and the fluid-taking piece, where the shielding body is C-shaped, according to an embodiment of the present disclosure.

The present disclosure will be further described in detail below in conjunction with FIGS. 3, 40 and 41.

A disposable sealed body fluid retention device includes a fluid storage tube 1, a fluid-taking piece 2 and a shielding body 4.

The fluid storage tube 1 includes an opening 11 and a fluid storage cavity 12, internal threads 14 are provided at the inner wall of the opening 11 of the fluid storage tube 1, and a plug part 5 is arranged on the lower part 13 of the fluid storage tube.

The fluid-taking piece 2 includes a fluid guiding passage 21, an air exhaust passage 22 and an annular side wall 23. The fluid guiding passage 21 has its upper end as a liquid inlet 24 and its lower end as a liquid outlet 25. The air exhaust passage 22 has its upper end as an air outlet 27 and its lower end as an air exhaust opening 26. The fluid guiding passage 21 and the air exhaust passage 22 are separated from each other by the spacer 28, a spacer extension 29 is formed by extending downwards from the spacer 28, and the lowest end of the spacer extension 29 is lower than the air exhaust opening 26 and the liquid outlet 25. The air exhaust opening 26 and the liquid outlet 25 are located on the lower end face 36 of the lower part 30 of the fluid-taking piece.

An annular step 32 is provided at the lower part 30 of the fluid-taking piece, and includes a first side face 321, a second side face 322 and a step surface 323 which is connected to both the first and second side faces 321 and 322. The second side face is adjacent to the lower end face 36. External threads 31 are provided on the second side face 322.

The fluid-taking piece 2 includes a handle 33, a holding portion 331 of which is disposed higher than the top of the annular side wall 23. A liquid collecting plate 6 may be fixed on the top of the annular side wall 23 at both sides of the handle 33.

The shielding body 4 has a C-shape surrounding the fluid storage tube at an angle of 300°, is positioned on the lower part 30 of the fluid-taking piece and attached thereto by magnetic adsorption. That is, the shielding body 4 is attached to the first side face 321 by magnetic adsorption. Alternatively, the shielding body 4 may be formed in one piece with the fluid-taking piece.

In the fluid taking process, the plug part 5 is arranged on the lower part of the fluid storage tube 1, and when the fluid taking process is completed, the plug part 5 on the fluid storage tube 1 is held by one hand and the fluid-taking piece 2 is removed, and subsequently the plug part 5 attached to the lower part of the fluid storage tube 1 is removed and mounted on the opening 11 to seal the same.

Eighth Embodiment

The present disclosure will be further described in detail below in conjunction with FIGS. 1, 4, 5, 6, 12, 15, 16, and 17 to 22.

A disposable sealed body fluid retention device includes a fluid storage tube 1, a fluid-taking piece 2, a shielding body 4, a plug part 5, a fluid collecting plate 6, and a connector 7.

The lower part 30 of the fluid-taking piece is fixedly connected to the through hole 70 of the connector 7, and the annular step 71 of the connector 7 is fixedly connected to the opening 11 of the fluid storage tube 1.

The Fluid Storage Tube 1 May Employ the Structure Described Below in the Present Embodiment.

As shown in FIG. 3, the fluid storage tube 1 includes an opening 11 and a fluid storage cavity 12, and internal threads 14 are provided on the inner wall of the opening 11 of the fluid storage tube 1.

As shown in FIG. 4, the fluid storage tube 1 includes an opening 11 and a fluid storage cavity 12, and internal threads 14 are provided on the inner wall of the opening 11 of the fluid storage tube 1. A plug part 5 is connected to the outer wall of the fluid storage tube 1, and may be formed in one piece with the fluid storage tube 1. Six longitudinal ribs 6 are arranged on the outer wall of the lower part 13 of the fluid storage tube 1. Alternatively, as shown in FIG. 6, eight longitudinal ribs 6 may be illustratively arranged on the outer wall of the lower part 13 of the fluid storage tube 1.

As shown in FIG. 5, the fluid storage tube 1 includes an opening 11 and a fluid storage cavity 12, and internal threads 14 are provided on the inner wall of the opening 11 of the fluid storage tube 1. A plug part 5 is connected to the outer wall of the fluid storage tube 1, and may be formed in one piece with the fluid storage tube 1. A plurality of protrusions 17 are arranged on the outer wall of the lower part 13 of the fluid storage tube 1.

The lower part 13 of the fluid storage tube 1 may have a cross section of a polygonal shape, for example, a pentagonal, hexagonal or octagonal shape. Alternatively, the fluid storage tube 1 may have a cross section of a polygonal shape, for example, a hexagonal or octagonal shape.

The provision of the skidproof structure, such as the ribs, protrusions, skidproof patterns and coarse surfaces, on the lower part 30 of the liquid storage tube is advantageous for easy holding of the liquid storage tube 1 being separated from the fluid-taking piece 2 after the fluid taking process has completed and for easy applying of forces to separate the fluid-taking piece 2 from the liquid storage tube 1.

The plug part 5 may employ the structure described below in the present embodiment.

As shown in FIGS. 2 and 14, the lower part 13 of the liquid storage tube 1 is inserted into the plug part 5.

As shown in FIGS. 4, 5, 11 and 13, the plug part 5 is connected to the outer wall of the liquid storage tube 1 and is formed in one piece with the liquid storage tube 1.

The Fluid-Taking Piece 2 May Employ the Structure Described Below in the Present Embodiment.

As shown in FIG. 1, the fluid-taking piece 2 includes a fluid guiding passage 21, an air exhaust passage 22, a spacer 28, an annular side wall 23 and a handle 33. The fluid guiding passage 21 and the air exhaust passage 22 are separated from each other by the spacer 28 within the annular side wall 23. The fluid guiding passage 21 has one end as a liquid inlet 24 and the other end as a liquid outlet 25, the air exhaust passage 22 has one end as an air outlet 27 and the other end as an air exhaust opening 26, and the air exhaust opening 26 and the liquid outlet 25 are at different planes and preferably the air exhaust opening 26 is at a higher level than the liquid outlet 25. A holding portion 331 of the handle 33 is disposed higher than the top of the annular side wall 23. A liquid collecting plate 6, which is used for collecting urine into the fluid guiding passage to avoid spurting of the urine to outside of the fluid-taking piece 2, is fixed to the top of the annular side wall 23 of the fluid-taking piece 2. The liquid collecting plate 6 may be arranged at both sides of the handle 33, or at either side of the handle 33. Alternatively, the liquid collecting plate 6 may be omitted. An anti-spurting layer may be disposed on the fluid guiding passage 21 of the fluid-taking piece 2 to suppress the spurting of urine in the fluid-taking process. A spacer extension 29, which is extended downwards from the spacer 28, is arranged between the air exhaust opening 26 and the liquid outlet 25 to prevent liquid from entering into the air exhaust opening 26. External threads 37 are provided on the outer wall of the lower part of the fluid-taking piece. A shielding side wall 45 of the shielding body 4 may be formed in one piece with the fluid-taking piece 2, and may have a tubular shape surrounding the fluid storage tube at an angle of 360°. The shielding body 4 is posited at the outside of the fluid storage tube 1, and the bottom of the fluid storage tube 1 is lower than the lowest portion of the shielding body 4. As shown in FIG. 12, the shielding side wall 45 of the shielding body 4 is formed in one piece with the lower part 30 of the fluid-taking piece and has a C-shape (i.e. a sector shape) surrounding the fluid storage tube at an angle of 340°, and the shielding body 4 is positioned at the outside of the fluid storage tube 1.

The Connector 7 May Employ the Structure Described Below in the Present Embodiment.

Figure 15:
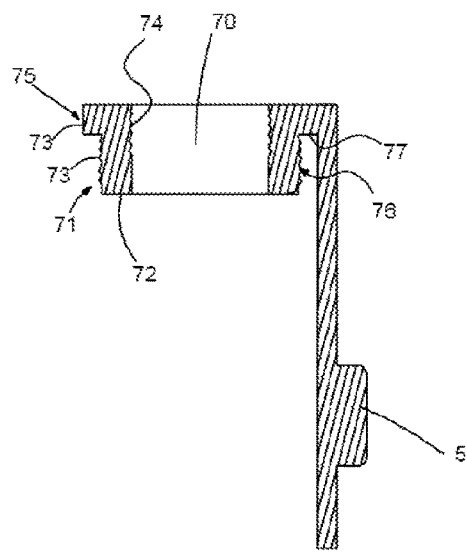
FIG. 15 schematically shows that a connecting piece 7 and a plug part 5 are formed in one piece and external threads 73 are provided on a second annular side wall 76 according to an embodiment of the present disclosure.

As shown in FIG. 15, the connector 7 includes an axial through hole 70, the wall of which is provided with internal threads 74. An annular step 71 is provided along the outer wall of the connector 7 from the lower end face 72 of the connector 7, and includes a first annular side wall 75, a step surface 77 and a second annular side wall 76. The first annular side wall 75 is folded in a direction to the center of the connector 7 to form the step surface 77, the step surface 77 is folded downwards to form the second annular side wall 76, and the second annular side wall 76 is adjacent to the lower end face 72. External threads 73 are formed on the second annular side wall 76. A plug part 15 is disposed on the first annular side wall 75 of the connector 7, and may be formed in one piece with the connector 7.

Figure 16:
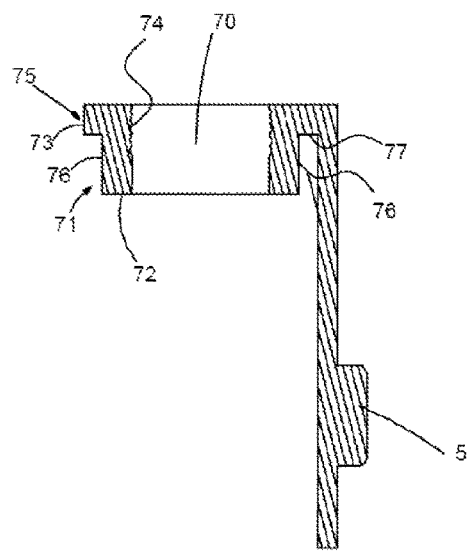
FIG. 16 schematically shows that a connecting piece 7 and a plug part 5 are formed in one piece, without external threads provided on the second annular side wall 76, according to an embodiment of the present disclosure.
Figure 17:
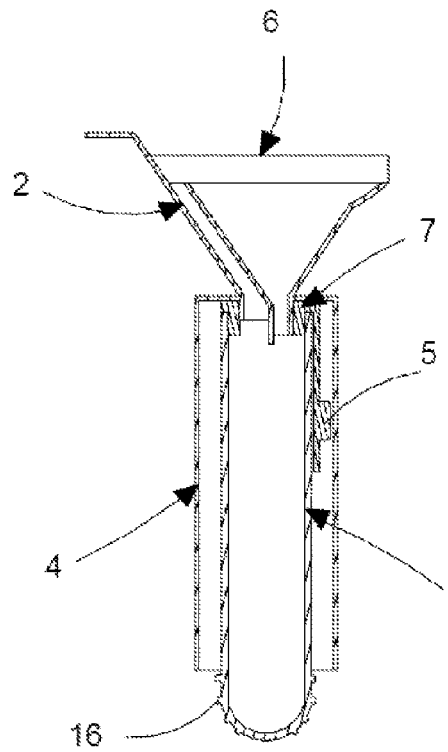
FIG. 17 schematically shows that a connecting piece is fixedly attached to the fluid-taking piece and the fluid storage tube, respectively, the shielding body has a tubular shape and is formed in one piece with the fluid-taking piece, protrusions are provided on the lower part of the fluid storage tube, and the connecting piece is formed in one piece with the plug part, according to an embodiment of the present disclosure.
Figure 18:
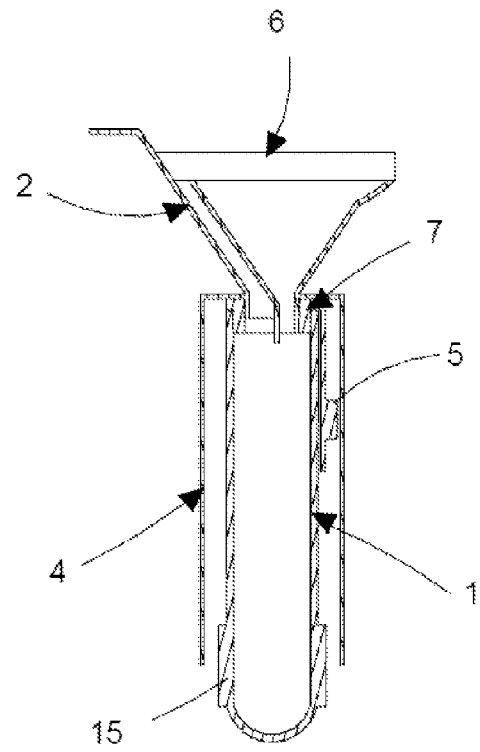
FIG. 18 schematically shows that a connecting piece is fixedly attached to the fluid-taking piece and the fluid storage tube, respectively, the shielding body has a tubular shape and is formed in one piece with the fluid-taking piece, longitudinal ribs are provided on the outer wall of the lower part of the fluid storage tube, and the connecting piece is formed in one piece with the plug part, according to an embodiment of the present disclosure.
Figure 19:
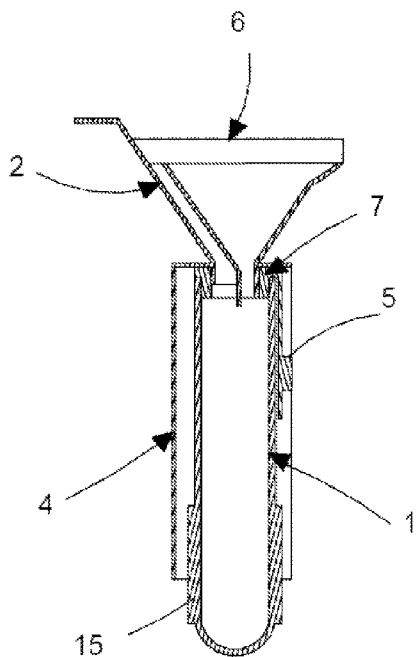
FIG. 19 schematically shows that a connecting piece is fixedly attached to the fluid-taking piece and the fluid storage tube, respectively, the shielding body is C-shaped and is formed in one piece with the fluid-taking piece, longitudinal ribs are provided on the outer wall of the lower part of the fluid storage tube, and the connecting piece is formed in one piece with the plug part, according to an embodiment of the present disclosure.
Figure 20:
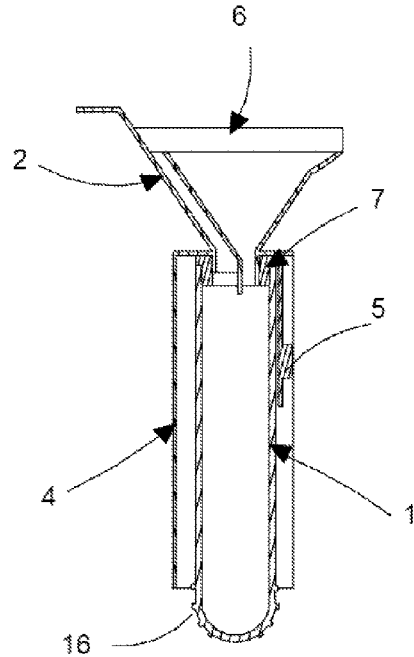
FIG. 20 schematically shows that a connecting piece is fixedly attached to the fluid-taking piece and the fluid storage tube, respectively, the shielding body is C-shaped and is formed in one piece with the fluid-taking piece, protrusions are provided on the lower part of the fluid storage tube, and the connecting piece is formed in one piece with the plug part, according to an embodiment of the present disclosure.
Figure 21:
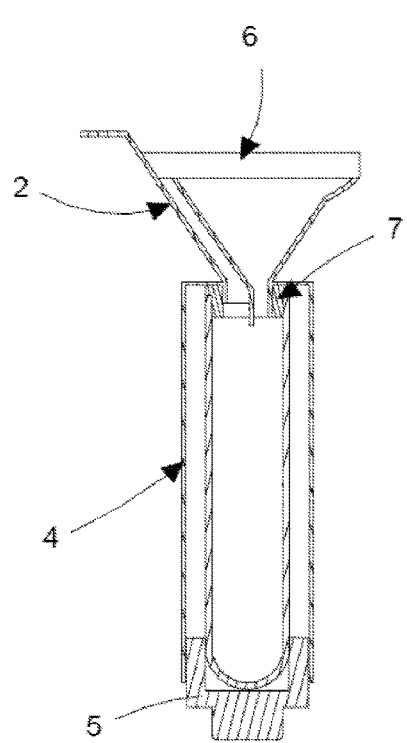
FIG. 21 schematically shows that a connecting piece is fixedly attached to the fluid-taking piece and the fluid storage tube, respectively, the shielding body has a tubular shape and is formed in one piece with the fluid-taking piece, longitudinal ribs are provided on the outer wall of the lower part of the fluid storage tube, and the plug part is provided at the lower end of the fluid storage tube, according to an embodiment of the present disclosure.
Figure 22:
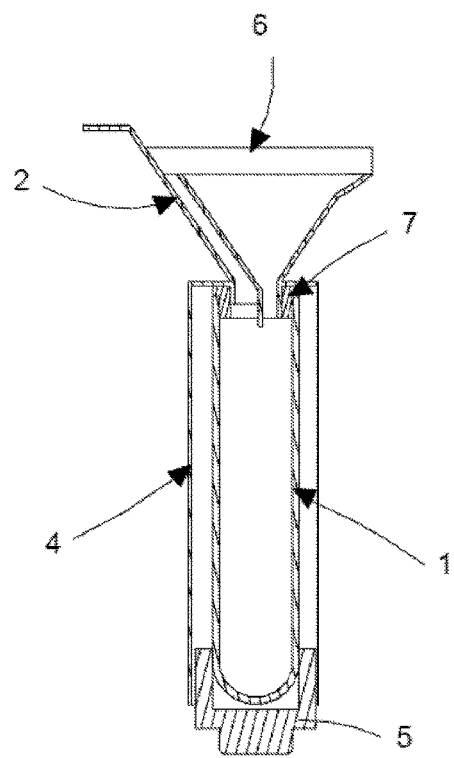
FIG. 22 schematically shows that a connecting piece is fixedly attached to the fluid-taking piece and the fluid storage tube, respectively, the shielding body is C-shaped and is formed in one piece with the fluid-taking piece, longitudinal ribs are provided on the outer wall of the lower part of the fluid storage tube, and the plug part is provided at the lower end of the fluid storage tube, according to an embodiment of the present disclosure.
Figure 23:
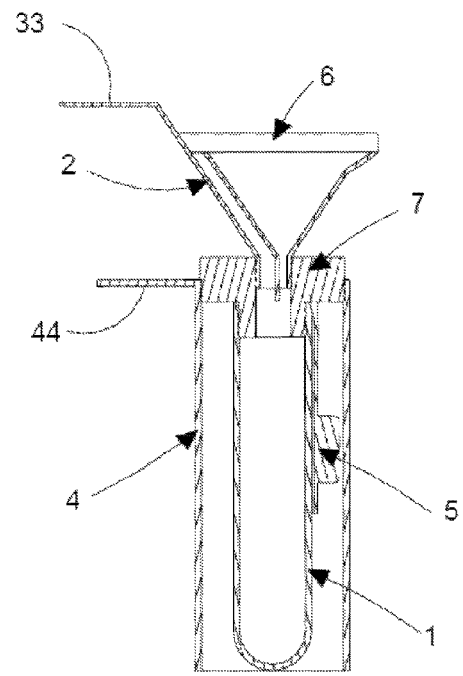
FIG. 23 schematically shows a body fluid retention device provided with a connecting piece, according to an embodiment of the present disclosure.

As shown in FIG. 16, the connector 7 includes an axial through hole 70, the wall of which is provided with internal threads 74. An annular step 71 is provided along the outer wall of the connector 7 from the lower end face 72 of the connector 7, and includes a first annular side wall 75, a step surface 77 and a second annular side wall 76. The first annular side wall 75 is folded in a direction to the center of the connector 7 to form the step surface 77, the step surface 77 is folded downwards to form the second annular side wall 76, and the second annular side wall 76 is adjacent to the lower end face 72. A plug part 15 is disposed on the first annular side wall 75 of the connector 7, and may be formed in one piece with the connector 7.

The through hole 70 shown in FIG. 15 or 16 may not be provided with internal threads.

The connector 7 may be made of elastic material such as silicone, rubber and TPU (Thermo Plastic Urethane), to facilitate the connection and sealing between the opening 11 of the fluid storage tube 1 and the connector 7.

The Liquid Collecting Plate 6 and the Fluid-Taking Piece 2 May be Fixedly Connected in a Manner as Described Below in the Present Embodiment.

The liquid collecting plate 6, which is used for collecting urine into the fluid guiding passage to avoid spurting of the urine to outside of the fluid-taking piece 2, is fixed to the top of the annular side wall 23 of the fluid-taking piece 2. The liquid collecting plate 6 may be arranged at both sides of the handle 33, or at either side of the handle 33. Alternatively, the liquid collecting plate 6 may be omitted.

An anti-spurting layer may be disposed on the fluid guiding passage 21 of the fluid-taking piece 2 to absorb the impact by the urine in the fluid-taking process, thereby eliminating urine spurted to the outside of the fluid-taking piece 2.

In the present embodiment, as shown in FIGS. 17 to 22, the external threads 73 on the outer wall of the lower part 30 of the fluid-taking piece cooperate with the internal threads 74 of the through hole 70, and the external threads 73 on the annular step 71 of the connector 7 cooperate with the internal threads 14 on the inner wall of the opening 11 of the fluid storage tube 1. In the case where the connector 7 employs the structure shown in FIG. 16, the connector 7 is insertedly connected to the fluid storage tube, that is, the second annular side wall 76 of the annular step 71 of the connector 7 tightly cooperates with the inner wall of the opening of the fluid storage tube 1.

The lower part 30 of the fluid-taking piece is detachably connected with the through hole 70, that is, the external threads 31 on the lower part 30 of the fluid-taking piece cooperate with the internal threads 74 of the through hole 70. Alternatively, the lower part 30 of the fluid-taking piece may be fixedly connected with the through hole 70, for example, by the interference fit, fastening, insertion or adhesive (or by threads or thread adhesive) between the lower part 30 of the fluid-taking piece and the through hole 70. Both the air exhaust opening 26 and the liquid outlet 25 are in communication with the through hole 70. In the case where the lower part 30 of the fluid-taking piece is insertedly connected with the through hole 70, the wall of the through hole 70 of the connector 7 may be provided with or without internal threads.

Figure 31:
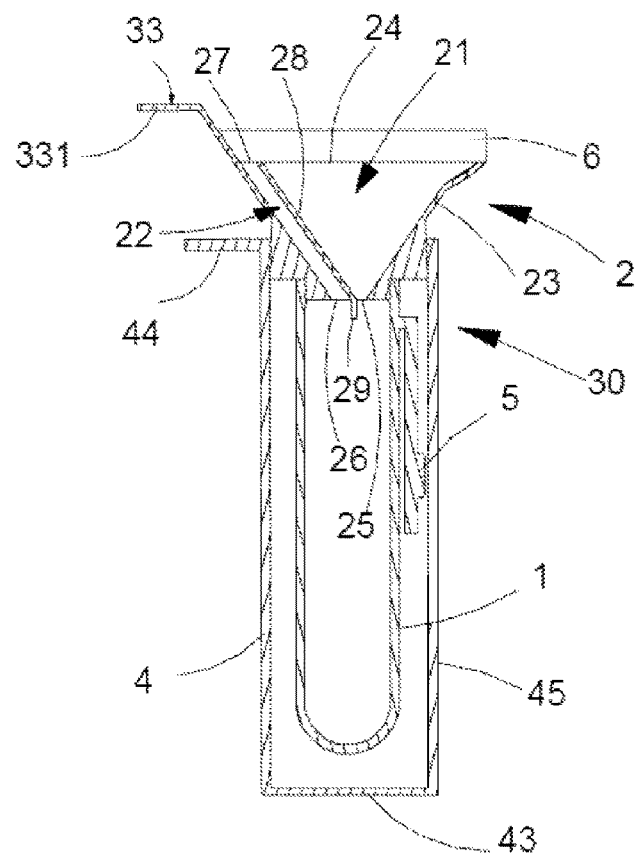
FIG. 31 schematically shows that the plug part and the fluid storage tube are formed in one piece, and the fluid-taking piece, the shielding body and the fluid storage tube are threadedly connected, according to an embodiment of the present disclosure.
Figure 32:
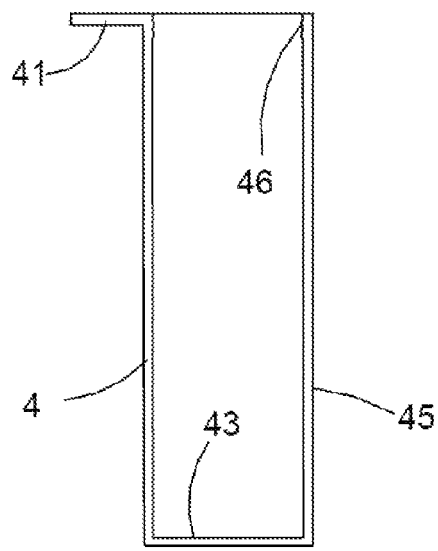
FIG. 32 schematically shows that the shielding body has a tubular shape and internal threads are provided on the inner side of the upper end of the shielding body according to an embodiment of the present disclosure.
Figure 33:
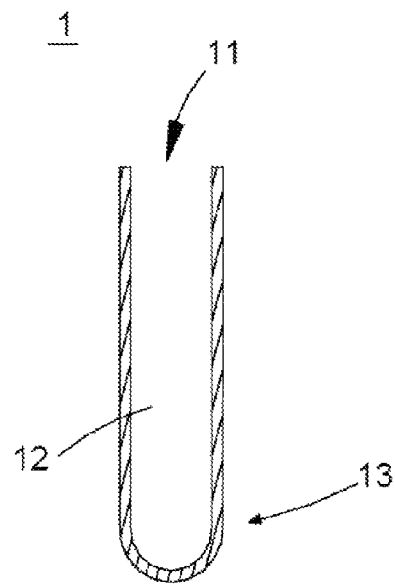
FIG. 33 schematically shows the tubular shape of the fluid storage tube according to an embodiment of the present disclosure.
Figure 34:
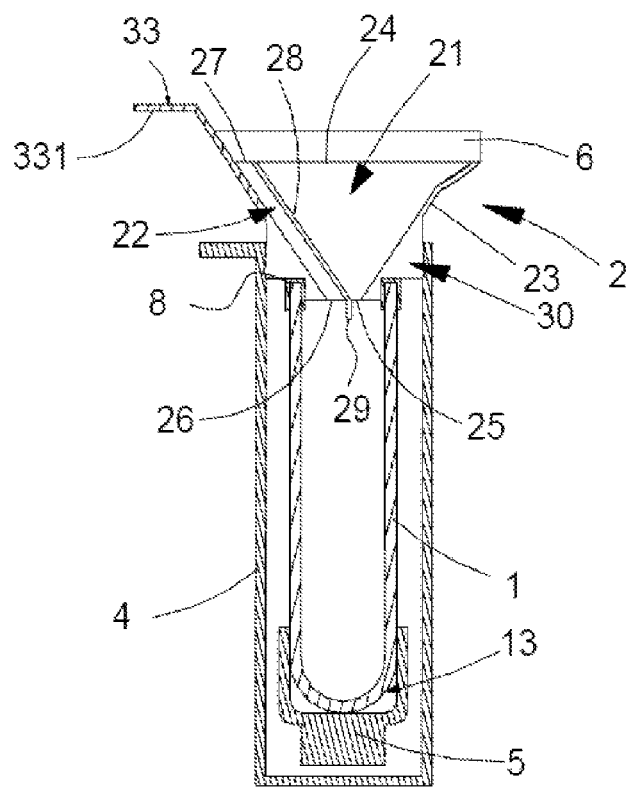
FIG. 34 schematically shows the insertion of the fluid storage tube into the fluid-taking piece and the threaded connection between the fluid-taking piece and the shielding body, according to an embodiment of the present disclosure.
Figure 35:
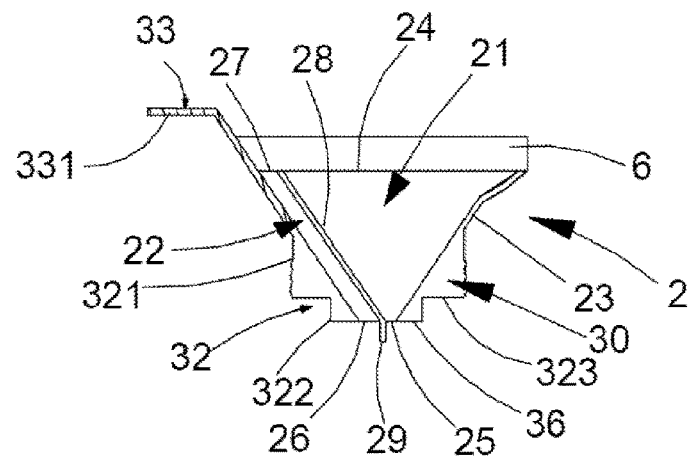
FIG. 35 schematically shows the arrangement of threads and an annular step at the lower part of the fluid-taking piece according to an embodiment of the present disclosure.

To collect the urine, the fluid-taking piece 2 is aligned with an outlet where fluid such as urine leaks. After a certain amount of the urine has been collected, as shown in FIGS. 17 to 20, the handle 33 is held by one hand while the lower part 13 of the fluid storage tube is held by the other hand, the fluid-taking piece 2 and the shielding body 4 are removed, and the plug part 5 is placed to match with the through hole 70 of the connector 7, so that the fluid storage cavity 12 of the fluid storage tube 1 is isolated from the outside. As shown in FIGS. 31 and 32, after the fluid collecting process is completed, the handle 33 is held by one hand while the handle 44 is held by the other hand, and the shielding body 4 is separate from the fluid-taking piece 2, subsequently the fluid-taking piece is separated from the fluid storage tube, and finally the plug part is mounted onto the opening of the fluid storage tube.

Figure 24:
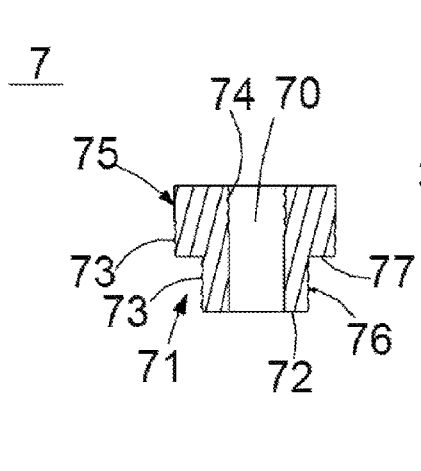
FIG. 24 schematically shows the connecting piece according to an embodiment of the present disclosure.
Figure 25:
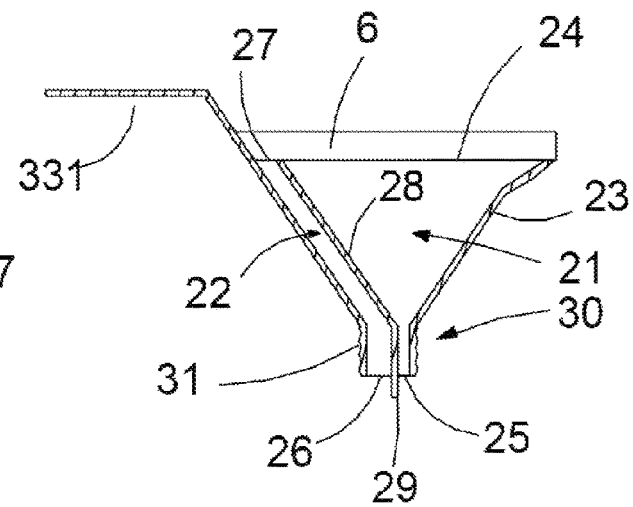
FIG. 25 schematically shows the fluid-taking piece according to an embodiment of the present disclosure.
Figure 30:
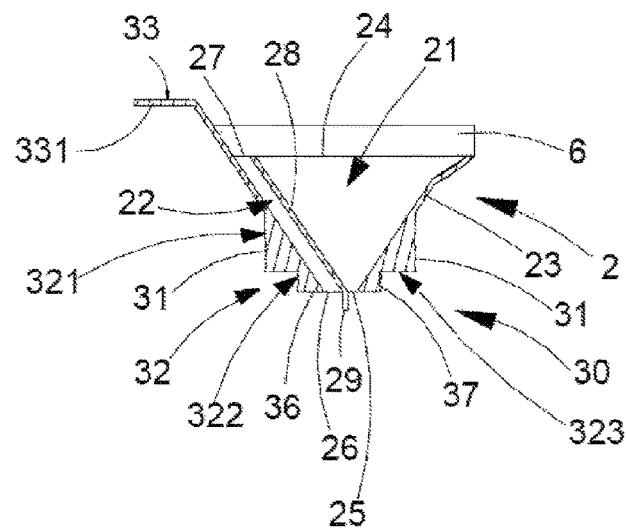
FIG. 30 schematically shows that the fluid-taking piece is provided with an annular step, a first side face and a second side face of which are provided with external threads, according to an embodiment of the present disclosure.

In the present embodiment, when the fluid storage tube 1 is formed in one piece with the plug part 5, the connector may employ the structure as shown in FIG. 24, in which the through hole 70 may be provided with or without internal threads 74. In the case where the through hole 70 is not provided with internal threads, the lower part 30 of the fluid-taking piece is insertedly connected with the through hole 70 of the connector 7. The second annular side wall 76 may be provided with or without external threads 73. In the case where the second annular side wall 76 is not provided with external threads, the opening 11 of the fluid storage tube 1 is insertedly connected with the annular step 71 of the connector 7.

COMPARATIVE EXAMPLES

1. Comparison in the Perspective of Components and Structures

In the present disclosure, there are two components, i.e. the fluid storage tube and the fluid-taking piece 2 with a shielding body.

During the urine collecting process, the fluid storage tube and the shielding body are connected as an integral structure.

After the urine collecting process is completed, the fluid storage tube is separated from the fluid-taking piece.

In the related art, there are two individual components, i.e. a urine accommodating cup and a fluid storage tube.

Conclusion: in the related art, operations are complicated, and the fluid storage tube might be stained by urine when the urine is being transferred to the fluid storage tube. Therefore, the present disclosure is advantageous in sanitation.

2. Comparison in the Perspective of Steps of Fluid Collecting Process

In the present disclosure, there are three steps of collecting urine, removing the fluid-taking piece from the body fluid retention device, and mounting the plug part.

In the related art, there are five steps of collecting urine with a urine accommodating cup, taking a fluid storage tube, pouring the urine into the fluid storage tube, disposing the urine accommodating cup, and inserting a plug.

Conclusion: the present disclosure is advantageous for convenience compared with the related art.

3. Comparison in the Perspective of Time Required for Fluid Collecting Process

A testing method was conducted and evaluated by average time for fluid collecting by 50 people.

The average time is 21 seconds in the present disclosure while the average time is 33 seconds in the related art.

Conclusion: the time required for fluid taking is reduced to 64% of that in the related art, so that the convenience and speed is significantly improved compared with the related art.

4. Comparison in the Perspective of Spurting of Urine During Urine Collecting Process In the present disclosure, because a liquid collecting plate and an anti-spurting layer are disposed on the fluid-taking piece, the spurting of urine is effectively prevented, meanwhile the urine in the fluid storage tube does not leak during the process of collecting urine and transferring the urine to the fluid storage tube.

In the related art, because of the small opening of the fluid storage tube and the shallow urine accommodating cap, the urine might be spurted onto the fluid storage tube in transferring the urine from the urine accommodating cup to the fluid storage tube.

5. Comparison in the Perspective of Sanitation of Fluid Storage Tube During Fluid Collecting Process In the present disclosure, the fluid storage tube is protected by the annular shielding body at an angle of 360°, so that the sanitation of the fluid storage tube is fully ensured during the urine collecting process. Further, after the urine collecting process is completed, the fluid-taking piece is disposed along with the shielding body which is formed in one piece with the fluid-taking piece or fixedly connected with the fluid-taking piece, the cleanness and sanitation of the fluid storage tube is ensured.

In the related art, because no protection measure is taken in pouring the urine from the urine accommodating cup to the fluid storage tube, the urine is very likely poured onto the fluid storage tube, thereby staining the fluid storage tube.

Conclusion: the inventive device is advantageous in sanitation compared with the related art.

The invention claimed is:

1. A disposable sealed body fluid retention device, comprising: a fluid storage tube, a fluid-taking piece, a shielding body and a connector, wherein
the fluid storage tube comprises an opening and a fluid storage cavity,
the shielding body comprises a shielding side wall surrounding the fluid storage tube, which is configured to prevent body fluid from spurting onto outer wall of the fluid storage tube;
the fluid-taking piece comprises an annular side wall, wherein a spacer is disposed in the annular side wall, and the spacer is configured to separate a fluid guiding passage from an air exhaust passage within the annular side wall,
the fluid guiding passage has one end as a liquid inlet and the other end as a liquid outlet, wherein the liquid outlet is located at a lower part of the fluid-taking piece; the air exhaust passage has one end as an air outlet and the other end as an air exhaust opening, and the air exhaust opening is located at the lower part of the fluid-taking piece, the lower part of the fluid-taking piece is detachably and sealedly connected with the opening of the fluid storage tube;
wherein the connector comprises an axial through hole, the lower part of the fluid-taking piece is fixedly connected to the through hole of the connector, the connector is detachably and fixedly connected to the opening of the fluid storage tube, and both the air exhaust opening and the liquid outlet are in communication with the through hole.

2. The disposable sealed body fluid retention device of claim 1, wherein
an annular step is provided along an outer wall of the connector from a lower end face of the connector, and comprises a first annular side wall, a step surface and a second annular side wall, the first annular side wall is folded in a direction to the center of the connector to form the step surface, the step surface is folded downwards to form the second annular side wall, the second annular side wall is adjacent to the lower end face, and external threads are formed on the first annular side wall and the second annular side wall, respectively,
internal threads are provided on an inner wall of the opening of the fluid storage tube, and
the external threads on the second annular side wall match with the internal threads on the inner wall of the opening of the fluid storage tube.

3. The disposable sealed body fluid retention device of claim 1, wherein a sealing ring is disposed between the lower part of the fluid-taking piece and the opening of the fluid storage tube.

4. The disposable sealed body fluid retention device of claim 1, wherein a spacer extension is extended downward from the spacer between the liquid outlet and the air exhaust opening, and the lowest end of the spacer extension is lower than the lowest end of the air exhaust opening and the liquid outlet, to prevent liquid from entering into the air exhaust opening from the liquid outlet.

5. The disposable sealed body fluid retention device of claim 4, further comprising a plug part, which is configured to match with the opening of the fluid storage tube and to close the fluid storage tube to isolate the fluid storage tube from the outside.

6. The disposable sealed body fluid retention device of claim 5, wherein the plug part is further configured to be detachably connected to the side wall of the lower part of the fluid storage tube.

7. The disposable sealed body fluid retention device of claim 4, wherein the fluid-taking piece comprises a handle, which is located at the same side as the air exhaust opening of the air exhaust passage.

8. The disposable sealed body fluid retention device of claim 4, wherein the air exhaust opening is disposed higher than the liquid outlet.

9. The disposable sealed body fluid retention device of claim 1, further comprising a plug part, which is configured to match with the opening of the fluid storage tube and to close the fluid storage tube to isolate the fluid storage tube from the outside.

10. The disposable sealed body fluid retention device of claim 9, wherein the plug part is further configured to be detachably connected to the side wall of the lower part of the fluid storage tube.

11. The disposable sealed body fluid retention device of claim 1, wherein the fluid-taking piece comprises a handle, which is located at the same side as the air exhaust opening of the air exhaust passage.

12. The disposable sealed body fluid retention device of claim 11, wherein the air exhaust opening is disposed higher than the liquid outlet.

13. The disposable sealed body fluid retention device of claim 1, wherein the air exhaust opening is disposed higher than the liquid outlet.

14. The disposable sealed body fluid retention device of claim 1, wherein the lower part of the fluid-taking piece is detachably connected with the through hole.

* * * * *